United States Patent
Hasegawa et al.

[11] Patent Number: 5,240,934
[45] Date of Patent: Aug. 31, 1993

[54] QUINOLINE DERIVATIVES

[75] Inventors: Hiroshi Hasegawa, Sakura; Kazuo Isomae; Takeshi Kotsugai, both of Narita; Noriaki Shioiri, Chiba; Kumiko Sekine, Narita; Naokata Taido, Funabashi; Susumu Sato, Inba; Tadayuki Kuraishi, Chiba, all of Japan

[73] Assignee: SS Pharmaceutical Co., Ltd., Tokyo, Japan

[21] Appl. No.: 946,620

[22] Filed: Sep. 18, 1992

Related U.S. Application Data

[62] Division of Ser. No. 773,432, Oct. 9, 1991, Pat. No. 5,190,951.

[30] Foreign Application Priority Data

Oct. 19, 1990 [JP] Japan .................. 2-281093
Oct. 19, 1990 [JP] Japan .................. 2-281094

[51] Int. Cl.$^5$ .................. C07D 401/04; C07D 401/06; C07D 471/04; A61K 31/55
[52] U.S. Cl. .................. 514/290; 514/292; 514/297; 546/79; 546/93; 546/104; 540/521; 540/580
[58] Field of Search .................. 546/79, 103, 104, 93, 546/105; 514/290, 297, 292; 540/521, 580

[56] References Cited

FOREIGN PATENT DOCUMENTS 0229391 7/1987 European Pat. Off. .
0296560 12/1988 European Pat. Off. .
0371388 6/1990 Japan .................. 546/105
2177692 1/1987 United Kingdom .

OTHER PUBLICATIONS

Journal of Medicinal Chemistry, vol. 32 No. 8 Aug. 8, 1989, pp. 1805–1813 American Chemical Society, Washington, D.C., US G. M. Shutske, et al., "9-Amino-1,2,3,4-Tetrahydroacridin-1-ols; Synthesis and Evaluation as Potential Alzheimer's Disease Therapeutics".

Sugimoto, H. *Novel Piperidine Derivatives Synthesis and Anti-Actylcholinesterase Activity of 1-Benzyl-4-[2-(-N-benzoylamino)ethyl]piperidine Derivatives*, J. Med. Chem. 1990 (33) 1880–1887.

*Primary Examiner*—Alan L. Rotman
*Assistant Examiner*—Phyllis G. Spivack
*Attorney, Agent, or Firm*—Oblon, Spivak, McClelland, Maier & Neustadt

[57] ABSTRACT

Quinoline derivatives of the formula,

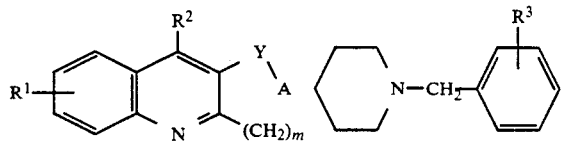

wherein $>A$ represents a group $>N-(CH_2)_n-$, $>C=$, $>C=CH(CH_2)_n-$, or $>CH(CH_2)_n-$, wherein n is an integer of 0–7; Y represents a group $>C=O$ or $>CHOH$, $R^1$ is a hydrogen atom, a halogen atom, an alkyl group, an alkoxy group, or an alkylthio group, $R^2$ is a hydrogen atom, a halogen atom, an alkyl group, a hydroxy group, an alkoxy group, a phenyl group which may have a substituent, a phenoxy group, an alkanoyloxy group, or an amino group which may have a substituent, $R^3$ is a hydrogen atom, a halogen atom, an alkyl group, or an alkoxy group, and m is an integer of 1–3. The compounds and their salts exhibit a superior anti-acetylcholinesterase activity with no side effects and are effective for the prevention or cure of senile dementia or memory disturbance.

4 Claims, No Drawings

QUINOLINE DERIVATIVES

This is a division of application Ser. No. 07/773,432, filed on Oct. 9, 1991, now U.S. Pat. No. 5,190,951.

BACKGROUND OF THE INVENTION

1. Field of the Invention

The present invention relates to a novel quinoline derivative and a salt thereof possessing a superior anti-acetylcholinesterase activity, an intermediate for the preparation of the quinoline derivative and a salt thereof, and a pharmaceutical composition comprising these compounds.

2. Description of the Background

Senile dementia is broadly classified into the cerebral vascular disorder type and the Alzheimer type. Even though causes of Alzheimer type senile dementia have still to be elucidated, a number of attempts have been undertaken to treat or cure the disease by the administration of cholinergic drugs, since the theory of the cholinergic effects was proposed. For example, there is a report on the study of curing senile dementia by the use of physostigmine which is a typical acetylcholinesterase inhibitor [Neurology, 8, 397 (1978)]. Japanese Patent Laid-open (Kokai) Nos. 148154/1986, 141980/1988, 166881/1988, 73/1989, 250353/1989, 167267/1990, J. Medicinal Chemistry, 31, 1278 (1988), and J. Medicinal Chemistry, 32, 1805 (1989) report about anti-acetylcholinesterase effects of aminoacridine derivatives, claiming the effectiveness of the compounds in the curing of senile dementia. Summers et al. report the effectiveness of 9-amino-1,2,3,4-tetrahydroacridine (Tacrine) and lecithin in the improvement in symptoms of senile dementia patients of Alzheimer type [The New England Journal of Medicine, 315, 1241 (1986)].

These known acetylcholinesterase inhibitors, however, do not exhibit sufficient curative effects and are accompanied by side effects such as liver disorders and the like.

The development of a compound useful as a medicine for curing dementia, which possesses an excellent anti-acetylcholinesterase effect with a least side effects, has therefore been desired.

In view of this situation, the present inventors synthesized various compounds and studied their pharmaceutical effects, and found that novel quinoline derivatives represented by the following formula (I) or their salts and novel piperidine derivatives represented by the following formula (II) or their salts exhibited excellent anti-acetylcholinesterase effects and were effective for curing dementia such as amnesic syndrome. Such a finding has led to the completion of this invention.

SUMMARY OF THE INVENTION

Accordingly, an object of the present invention is to provide a quinoline derivative represented by the following formula (I):

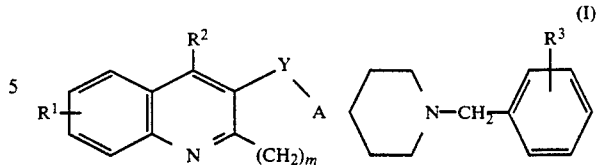

wherein $>A$ represents a group $>N-(CH_2)_n-$, $>C=$, $>C=CH(CH_2)_n-$, or $>CH(CH_2)_n-$, wherein n is an integer of 0–7; Y represents a group $>C=O$ or $>CHOH$, $R^1$ is a hydrogen atom, a halogen atom, an alkyl group, an alkoxy group, or an alkylthio group, $R^2$ is a hydrogen atom, a halogen atom, an alkyl group, a hydroxy group, an alkoxy group, a phenyl group which may have a substituent, a phenoxy group, an alkanoyloxy group, or an amino group which may have a substituent, $R^3$ is a hydrogen atom, a halogen atom, an alkyl group, or an alkoxy group, and m is an integer of 1–3; or a salt thereof.

Another object of the present invention is to provide a piperidine derivative represented by the following formula (II):

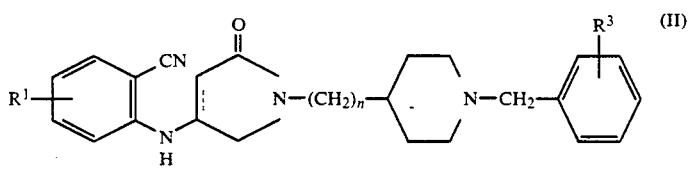

wherein $R^1$ is a hydrogen atom, a halogen atom, an alkyl group, an alkoxy group, or an alkylthio group, $R^3$ is a hydrogen atom, a halogen atom, an alkyl group, or an alkoxy group, n is an integer of 0–7, and the dotted line may optionally be present; or a salt thereof.

Still another object of the present invention is to provide a composition for inhibiting acetylcholinesterase comprising a quinoline of formula (I) or a salt thereof, or a piperidine derivative of formula (II) or a salt thereof, and a pharmaceutically acceptable carrier.

A further object of the present invention is to provide a method of preventing or treating dementia comprising administering an effective dose of a quinoline of formula (I) or a salt thereof, or a piperidine derivative of formula (II) or a salt thereof, to a person suffering from or under a risk of suffering from dementia.

Other objects, features and advantages of the invention will hereinafter become more readily apparent from the following description.

DETAILED DESCRIPTION OF THE INVENTION AND PREFERRED EMBODIMENTS

In the definition of formulae (I) and (II), the alkyl group is a linear, branched, or cyclic alkyl group having 1–8 carbon atoms, e.g., methyl, ethyl, n-propyl, i-propyl, n-butyl, i-butyl, t-butyl, n-pentyl, n-hexyl, cyclopropyl, cyclopentyl, cyclohexyl, etc.; the alkoxy group is an alkoxy group having 1–8 carbon atoms, e.g., methoxy, ethoxy, n-propoxy, i-propoxy, n-butoxy, i-butoxy, t-butoxy, etc.; the halogen atom is chlorine, bromine, or fluorine; the alkylthio group is an alkylthio group having 1–8 carbon atoms, e.g., methylthio, ethylthio, n-propylthio, n-butylthio, i-propylthio, etc.; and the alkanoyloxy group is an alkanoyloxy group having 2-6 carbon atoms, e.g., acetyloxy, propionyloxy, n-butyryloxy, i-butyryloxy, n-valeryloxy, i-valeryloxy, hexanoyloxy, etc. The phenyl group which may have a substituent is, for example, phenyl, o-methylphenyl, m-methylphenyl, p-methylphenyl, o-methoxyphenyl, m-methoxyphenyl, p-methoxyphenyl, etc. The groups which may be a substituent for the amino group include alkyl, aralkyl, aralkylaminoalkyl, alkanoyl, alkoxycarbonyl, (1-benzylpiperidine-4-yl)methyl, 2-(1-benzylpiperidine-4-yl)ethyl, 3-(1-benzylpiperidine-4-yl)propyl, 4-(1-benzylpiperidine-4-yl)butyl, etc. Here, the aralkyl groups are benzyl, o-xylyl, m-xylyl, p-xylyl, o-anisyl, m-anisyl, p-anisyl, o-fluorobenzyl, m-fluorobenzyl, p-fluorobenzyl, o-chlorobenzyl, m-chlorobenzyl, p-chlorobenzyl, o-fluoromethylbenzyl, m-fluoromethylbenzyl, p-fluoromethylbenzyl, phenetyl, etc. The alkanoyl groups are those containing 1-6 carbon atoms, e.g., acetyl, propionyl, n-butyryl, i-butyryl, n-valeryl, i-valeryl, n-hexanoyl, etc., and the alkoxycarbonyl groups are those containing 2-6 carbon atoms, e.g., methoxycarbonyl, ethoxycarbonyl, n-propoxycarbonyl, i-propoxycarbonyl, n-butoxycarbonyl, t-butoxycarbonyl, etc.

There are no specific restrictions as to the salts of compounds of formula (I) or (II), so long as they are pharmaceutically acceptable compounds. They may be a salt of inorganic acid, e.g., hydrochloride, sulfate, nitrate, hydrobromide, etc.; or a salt of organic acid, e.g., acetate, oxalate, citrate, fumarate, maleate, succinate, lactate, p-toluenesulfonate, methanesulfonate, etc.

The compound of formula (I) or (II) of the present invention can be prepared by one of the following processes 1-6.

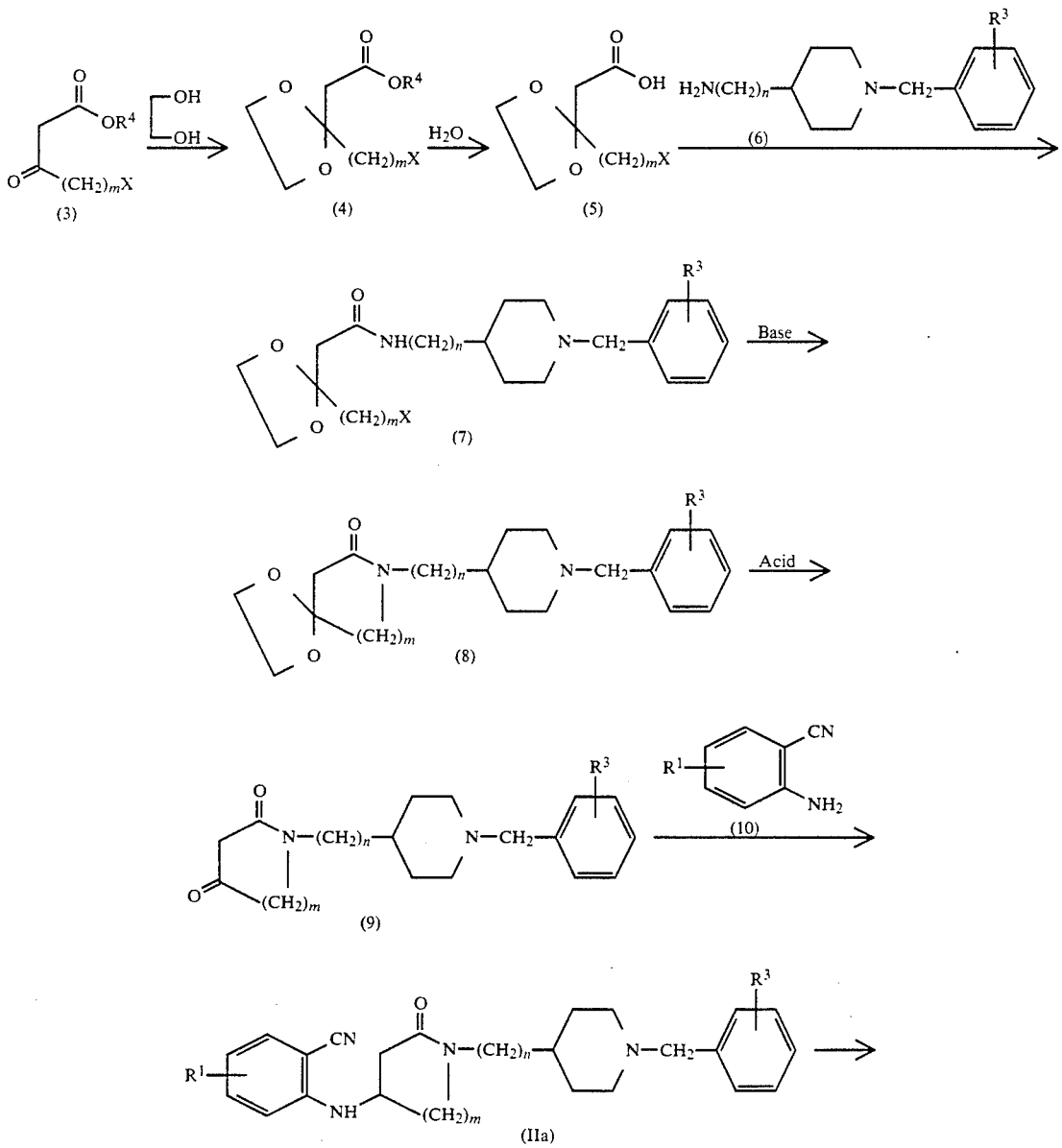

-continued (Process 1)

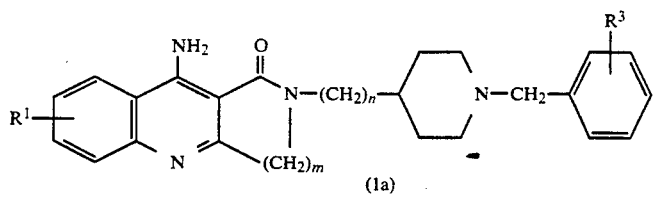

In the above reactions, X is a halogen atom, $R^4$ is a lower alkyl group, $R^1$, $R^3$, m and n are the same as those previously defined.

According to the above process, an ester of halogeno-$\beta$-keto acid (3) is reacted with ethylene glycol to obtain an ester of halogeno-$\beta$,$\beta$-ethylenedioxyalkanoic acid (4), which is hydrolyzed into halogeno-$\beta$,$\beta$-ethylenedioxyalkanoic acid (5). Compound (5) is then reacted with compound (6) to produce an amide compound (7), which is converted into a cyclic amide derivative (8) by the reaction with a base. Compound (8) is deprotected into compound (9). This cyclic compound (9) is reacted with substituted o-aminobenzonitrile (10) to produce compound (IIa), which is cyclized to give a quinoline derivative (Ia) of the present invention.

The reaction of compound (3) with ethylene glycol can be carried out according to a conventional method in a solvent such as toluene and in the presence of an acid such as p-toluenesulfonic acid. The hydrolysis of compound (4) is preferably performed in the presence of a base such as sodium hydroxide, potassium hydroxide, or the like at room temperature. The reaction of compound (5) with compound (6) can be carried out in an inert solvent such as methylene chloride, chloroform, or the like in the presence of a condensing agent such as dicyclohexylcarbodimide. Compound (7) is cyclized by the reaction with a base such as sodium alkoxide in a polarized solvent such as alcohol or the like. The reaction for removing the ethylenedioxy group of compound (8) is preferably carried out by the reaction of compound (8) with hydrochloric acid in a solvent such as water, alcohol, or the like. The reaction of compound (9) and substituted o-aminobenzonitrile (10) can be carried out in a solvent such as toluene or benzene and in the presence of a condensing agent such as p-toluenesulfonic acid under heating. Compound (IIa) thus obtained is easily converted into a quinoline derivative (Ia) of the present invention by the cyclization. This cyclization reaction is performed in a solvent such as tetrahydrofuran, 1,4-dioxane, 1,2-dimethoxyethane, diethylene glycol dimethyl ether, or the like in the presence of a base (e.g., potassium carbonate) and copper (I) chloride at room temperature to a refluxing temperature.

Compound (IIa) may be converted into a compound of the following formula (IIb) by the reduction using sodium cyanoborohydride, or the like.

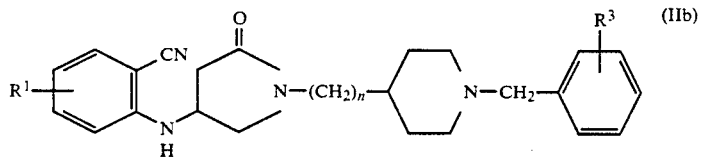

wherein $R^1$, $R^3$, m and n have the same meanings as previously defined.

(Process 2)

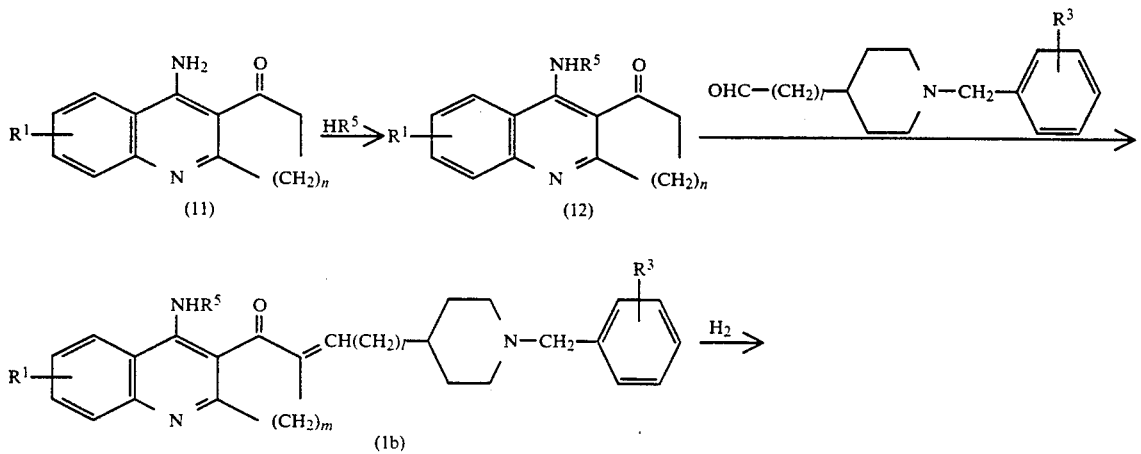

-continued
(Process 2)

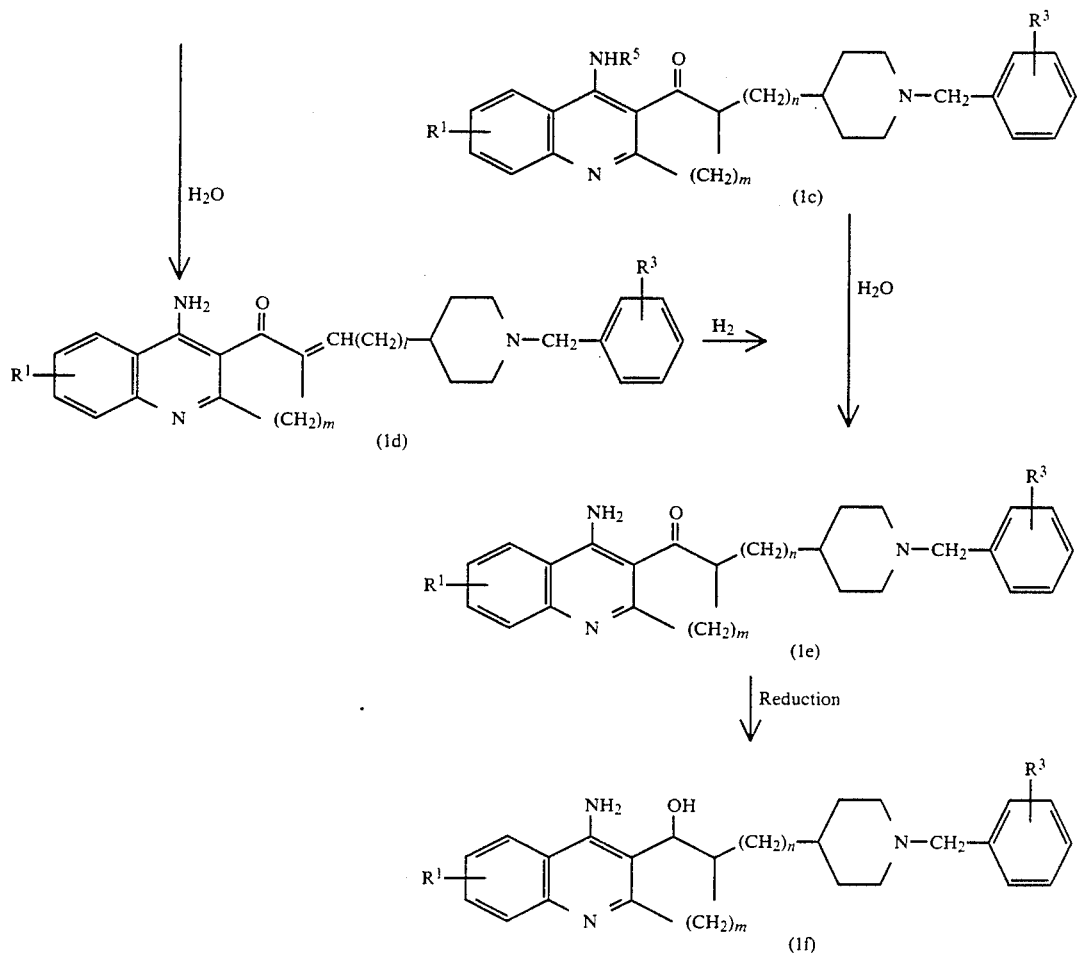

In the reaction scheme, $R^5$ is the above-mentioned group which may be a substituent for the amino group, 1 denotes an integer of 0-6, and $R^1$, $R^3$, m and n have the same meanings as previously defined.

According to the above reaction scheme, a quinoline derivative (11) is reacted with a compound $HR^5$, which is a reactive derivative of an alkyl formate or the like, to produce compound (12), followed by the reaction of compound (12) with an aldehyde compound (13) to give compound (Ib). Compound (Ib) can be reduced into compound (Ic). Compounds (Id) or (Ie) can be obtained by the hydrolysis of compounds (Ib) or (Ic), respectively. Compound (Ie) can be obtained also by the reduction of compound (Id), and a hydroxy compound (If) can be obtained by the reduction of (Ie).

Halogeno formate, acid anhydride formate, and the like are given as examples of the reactive derivative of an alkyl formate to be reacted with the quinoline derivative (11). The reaction of the quinoline derivative (11) and the formate is preferably carried out in a polarized solvent in the presence of a base such as 4-dimethylaminopyridine at room temperature to 80° C. The reaction of compounds (12) and (13) can be carried out in the presence of a base such as lithium diisopropylamide or the like at −80° C. to room temperature. The reduction of compound (Ib) or (Id) may be performed by feeding hydrogen in the presence of a conventional catalytic reducing agent, e.g. palladium carbon. The hydrolysis of compound (Ib) or (Ic) is carried out easily when $R^5$ is an alkoxycarbonyl group, in the presence of a mineral acid, e.g., hydrochloric acid, or an organic acid, e.g., trifluoro acetic acid. The reduction of compound (Ie) can be carried out by using sodium borohydride in a polarized solvent such as an alcohol, or by using lithium aluminum hydride in a solvent such as tetrahydrofuran.

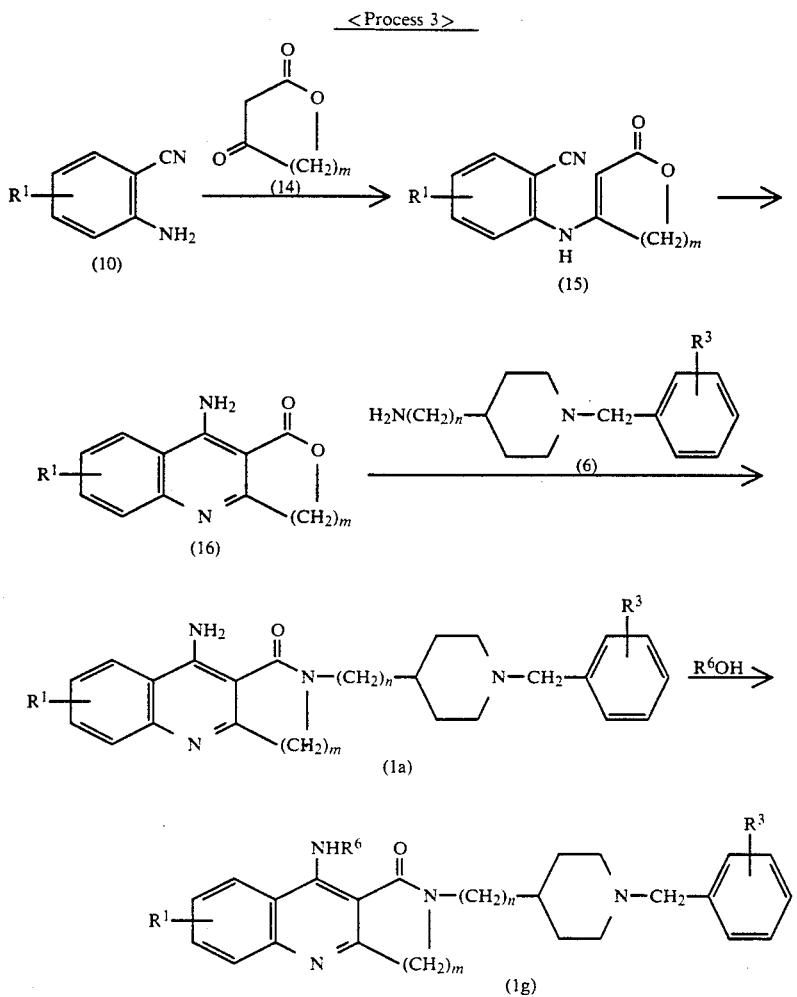

In the above reactions, $R^6$ is an alkanoyl group, and $R^1$, $R^3$, m and n have the same meanings as previously defined.

According to the reaction scheme, a β-ketolactone (14) of various kind is reacted with substituted o-aminobenzonitrile (10) to produce an enamine compound (15), which is then cyclized to give an aminoquinoline compound (16). The aminoquinoline compound (16) is then reacted with compound (6) to produce compound (Ia) of the present invention. Furthermore, the reaction of compound (Ia) with a reactive derivative of a fatty acid ($R^6$—OH) gives compound (Ig).

The reaction of substituted o-aminobenzonitrile (10) and β-ketolactone (14) can be carried out in an alcohol in the presence of an acid such as hydrochloric acid at room temperature, or in a solvent such as toluene or benzene and in the presence of a condensing agent such as p-toluenesulfonic acid under heating. The cyclization of enamine compound (15) is carried out in a solvent such as tetrahydrofuran, 1,4-dioxane, or the like in the presence of a base (e.g., potassium carbonate) and copper (I) chloride at room temperature to the refluxing temperature. The dehydration-condensation reaction of aminoquinoline compound (16) and compound (6) for producing quinoline derivative (Ia) may be carried out in the absence of a solvent, by tube at 100°-200° C. The reactive derivative of lower fatty acid to be reacted with compound (Ia) may be carboxylic acid anhydride, carboxylic acid halide, or the like, and the reaction can be effected in the presence of a base such as pyridine, triethylamine, or the like at room temperature to 100° C.

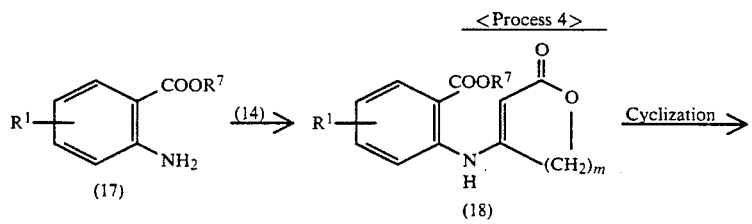

−continued
<Process 4>

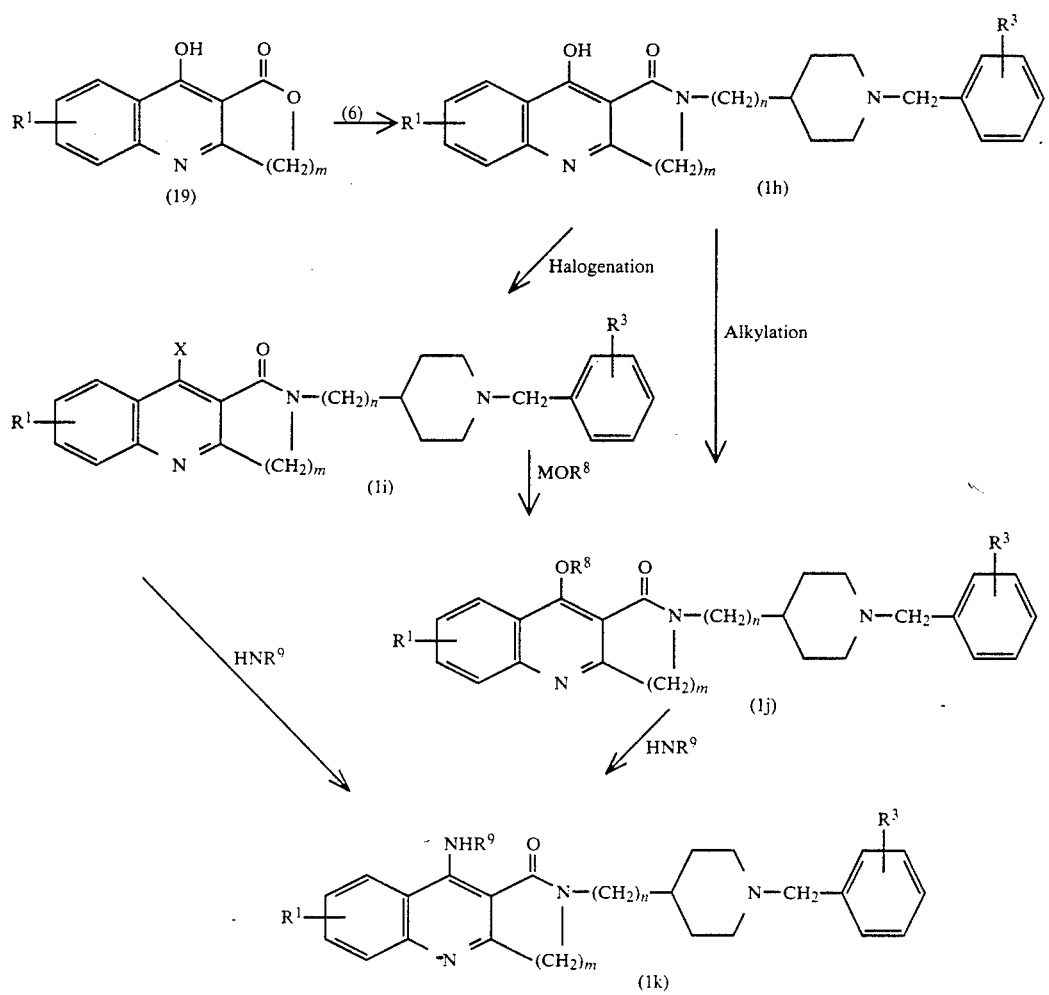

In the reaction scheme, $R^7$ is a hydrogen atom or an alkyl group, $R^8$ is an alkyl group or a phenyl group, $R^9$ is an alkyl group, a benzyl group which may have a substituent, or an aralkylaminoalkyl group, M is an alkali metal, X is a chlorine or bromine atom, and $R^1$, $R^3$, m and n have the same meanings as previously defined.

According to the above reaction scheme, β-ketolactone (14) of various kind is reacted with an anthranilic acid derivative (17) to produce enamine compound (18), which is then cyclized to give a quinolinol compound (19). This compound (19) is reacted with compound (6) to obtain quinoline derivative (Ih) of the present invention. Quinoline derivative (Ih) is halogenized to give compound (Ii) or alkylated into compound (Ij).

Compound (Ij) can also be prepared by reacting compound (Ii) with an alcoholate ($MOR^8$) of various kind. Compounds (Ii) and (Ij) may easily be converted into compound (Ik) by the reaction with an amine ($NHR^9$).

The cyclization of enamine compound (18) can be carried out by using polyphosphoric acid, trifluoromethane sulfonic acid, or a Lewis acid of various kinds, preferably by using polyphosphoric acid at 130°–150° C. The dehydration-condensation reaction of quinolinol compound (19) and compound (6) for producing quinoline derivative (Ih) may be carried out in a solvent such as N-methyl-2-pyrrolidone by heating the mixture to 180°–220° C. Compound (Ih) may be alkylated by using diazoalkane, or by the reaction with a lower-alkyl halide in a solvent such as dimethylsulfoxide, dimethylformamide, or the like and using sodium hydride as a base. The halogen substitution reaction of compound (Ih) can be carried out by using phosphorus oxychloride, triphenylphosphine dichloride, triphenylphosphine dibromide, or phosphorus pentachloride. The conversion of compound (Ii) to compound (Ij) can be carried out by reacting compound (Ii) with an alkaline metal salt of alcohol in a solvent such as an alcohol, dimethylformamide, or the like. Compounds (Ii) and (Ij) may easily be converted into compound (Ik) by the reaction of these compounds with an alkyl amine or a benzyl amine at room temperature to refluxing temperature.

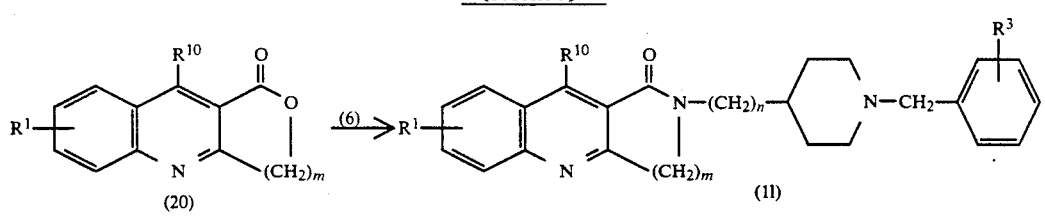

wherein $R^{10}$ is a hydrogen atom, an alkyl group, or a phenyl group which may have a substituent, and $R^1$, $R^3$, m and n have the same meanings as previously defined.

The reaction to produce quinoline derivative (II) of the present invention from compound (20) may be carried out in the same way as the reaction for producing compound (Ia) in Process 3.

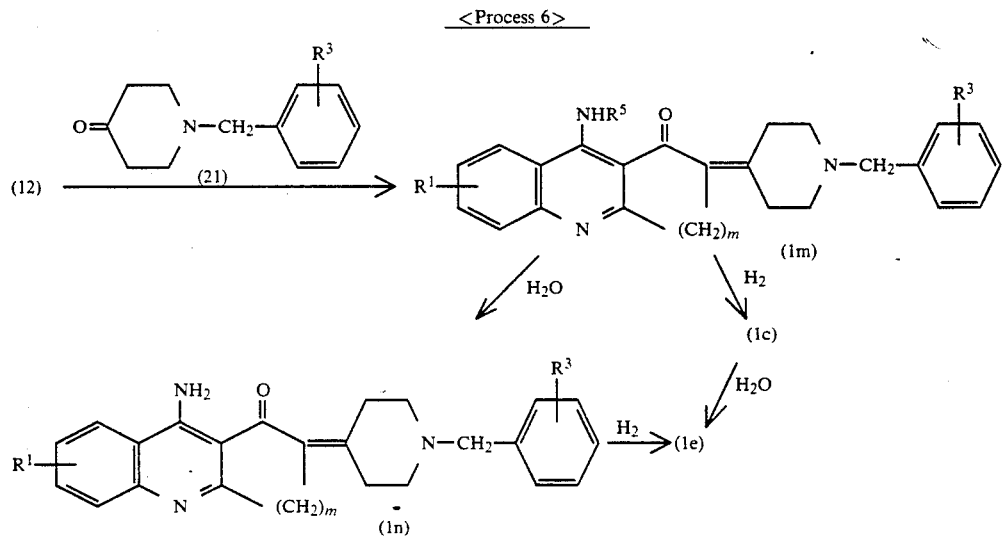

wherein $R^1$, $R^3$, $R^5$, and m have the same meanings as previously defined.

Carbonyl compound (21) is reacted with compound (12) to give compound (Im). Then, compounds (In), (Ic) and (Ie) can be prepared according to the same manner as in Process 2.

In the above processes, the separation of compound (I) of the present invention from the reaction mixture can be carried out by conventional methods such as solvent extraction, recrystallization, column chromatography, and the like.

Pharmacological Action of Compounds (I) and (II)

Pharmacological action of the compound of the present invention was tested using several compounds prepared in Examples presented hereinafter and 9-amino-1,2,3,4-tetrahydroacridine (Tacrine) as a comparative compound.

(A) Inhibitive Effect on Acetylcholinesterase Activity

The effects of the tested compounds on acetylcholinesterase activity were determined according to the method described in Biochemical Pharmacology, 7, 88, (1961).

$IC_{50}$: the concentration of the tested compound at which 50% of the control acetylcholinesterase activity was inhibited. Specific activities for the tested compounds were calculated using the following equation.

$$\text{Specific Activity} = \frac{IC_{50} \text{ of Tacrine}}{IC_{50} \text{ of Tested Compound}}$$

The results are shown in Table 1.

TABLE 1

| Compound No.* | Anti-acetylcholinesterase Activity (Specific Activity) |
|---|---|
| 2 | 7.7 |
| 3 | 13.5 |
| 7 | 1.94 |
| 14 | 5.00 |
| 46 | 47.62 |
| 67 | 9.52 |
| Tacrine | 1.00 |

*represents Compound No. in Examples.

(B) Effects on Amnesia Induced by Scopolamine in Mice

Male ddy mice, 6–7 week old, were used as subjects. A conventional two-compartment box was used for the passive avoidance test.

Tested compounds were given p.o. 30 minutes before scopolamine (1 mg/kg, i.p.). At 30 minutes after the scopolamine treatment, scrambled foot-schock (2 mA for 3 seconds) was applied to the mouse immediately after entry into the dark compartment. Retention was measured 6 hours after the training and was expressed as the mean latency to enter the dark compartment, with a cut-off point at 300 seconds. Percent improvement for the tested compounds were evaluated taking the difference between the retention latency of the untreated group and that of the control group as 100%.

The results are shown in Table 2.

TABLE 2

| Compound No. | Dose (mg/kg) | Percent Improvement |
| --- | --- | --- |
| 2 | 0.01 | 10.0 |
|  | 0.3 | 72.8 |
| 3 | 0.1 | 16.0 |
|  | 0.3 | 53.4 |
| 7 | 0.03 | 52.0 |
|  | 0.1 | 70.2 |
| 14 | 0.03 | 50.0 |
|  | 0.1 | 71.9 |
| Tacrine | 0.1 | 0 |
|  | 1.0 | 26.9 |

(C) Effects on Amnesia Induced by Scopolamine in Rats

Male Wister rats, 8 week old, were used as subjects. A conventional two-compartment box was used for the passive avoidance test.

Tested compounds were given p.o. 15 minutes after scopolamine hydrochloride (0.5 mg/kg, i.p.). At 15 minutes after the tested compound treatment, scrambled foot-schock (0.5 mA for 3 seconds) was applied to the rat immediately after entry into the dark compartment. Retention was measured 24 hours after the training and was expressed as the mean latency to enter the dark compartment, with a cut-off point at 600 seconds. Percent improvement for the tested compounds was evaluated taking the difference between the retention latency of the untreated group and that of the control group as 100%.

The results are shown in Table 3.

TABLE 3

| Compound No. | Dose (mg/kg) | Percent Improvement |
| --- | --- | --- |
| 7 | 0.03 | 36.1 |
|  | 0.1 | 68.9 |
|  | 0.3 | 69.8 |
| 14 | 0.1 | 0 |
|  | 0.3 | 50.8 |
| 46 | 0.1 | 32.3 |
|  | 0.3 | 39.1 |
| 61 | 0.03 | 33.0 |
|  | 0.1 | 86.1 |
|  | 0.3 | 86.5 |
| 67 | 0.03 | 50.4 |
|  | 0.1 | 92.0 |
|  | 0.3 | 95.8 |

As mentioned above, the compounds (I) and (II) of the present invention possess excellent anti-acetylcholinesterase activity, and exhibit a superior anti-dementia effect based on the anti-acetylcholinesterase These compounds induced no death in mice by the oral administration at a dose of 300 mg/kg.

Although a dose of the compound (I) or (II), or their salt, of the present invention, when used as an anti-dementia agent, depends on the weight, the age, the sex, the manner of administration, the physical conditions, or the symptom of the patient, a suitable amount is about 2 to 200 mg per day for oral administration, and about 0.2 to 20 mg per day for parenteral administration.

These compounds can be formed into various preparations, such as tablets, granules, powders, capsules, suspensions, injections, suppositories, preparations for external application, and the like according to known methods. In order to prepare solid preparations, excipients, and as required, binders, disintegrators, lubricants, coloring agents, sweetening agents, flavoring agents, fillers, coating agents, sugar-coating agents, and the like, are appropriately added to Compound (I) or (II) and the mixture is made into tablets, granules, powders, capsules, suppositories, or the like according to a conventional method. For formulating injection preparations, the compound is dissolved or dispersed into an aqueous medium such as distilled water, emulsified by the aqueous medium, or a powdery preparation may be dissolved when the injection is performed. Intravenous, intraarterial, intraportal, intraperitoneal, subcutaneous, or intramuscular injection are applicable to compound (I) or (II) of the present invention.

As mentioned above, the compounds (I) and (II) of the present invention possess strong anti-acetylcholinesterase activity, and exhibit an activity against scopolamine-induced amnesia models. They are effective for the prevention or cure of senile dementia or memory disturbance such as Alzheimer diseases.

Other features of the invention will become apparent in the course of the following description of the exemplary embodiments which are given for illustration of the invention and are not intended to be limiting thereof.

EXAMPLES

Reference Example 1

Ethyl 4-chloro-3,3-ethylenedioxybutanoate (15.63 gm) was dissolved in 150 ml of ethanol, and to the solution was dropwise added 75 ml of 2N potassium hydroxide. After stirring for 1 hour at room temperature, the resultant reaction mixture was concentrated under reduced pressure. Saturated brine was added to the concentrate, followed by cooling with ice water and addition of diluted hydrochloric acid to adjust pH to 3. The deposited crystals were collected by filtration and dried to obtain 11.97 gm of 4-chloro-3,3-ethylenedioxybutanoic acid.

mp 64°–65° C.

$^1$H-NMR $\delta$ ppm (CDCl$_3$) 4.09(s, 4H), 3.72(s, 2H), 2.91(s, 2H).

Reference Example 2

(1) 4-Chloro-3,3-ethylenedioxybutanoic acid (6.5 gm) was dissolved in 180 ml of dichloromethane, and to the solution was added 7.38 gm of dicyclohexylcarbodimide at 0° C. while stirring. After 15 minutes, 20 ml of dichloromethane solution containing 7.34 gm of 4-aminomethyl-1-benzylpiperidine was added dropwise. The mixture was stirred for 1 hour at 0° C. and 15 hours at room temperature. After the precipitate was filtered, the filtrate was washed with a saturated aqueous solution of sodium bicarbonate and with water, and dried, followed by evaporation of the solvent under reduced pressure. The residue was submitted to silica gel column chromatography to obtain 10.02 gm of N-(4-(1-benzylpiperidyl)methyl)-4-chloro- 3,3-ethylenedioxybutanoic acid amide from chloroform-methanol (20:1–15:1) fractions.

mp: 78°–79° C.

$^1$H-NMR $\delta$ ppm (CDCl3) 7.35(s, 5H), 6.23(br. 1H), 4.08(s, 4H), 3.61(s, 2H), 3.59(s, 2H), 3.15(b. t, 2H), 2.98(b. d, 2H), 2.71(s, 2H), 2.22–1.24(m, 7H).

(2) N-(4-(1-benzylpiperidyl)methyl)-4-chloro-3,3-ethylenedioxybutanamide (8.43 gm) was dissolved in 50 ml of 1M sodium ethoxide solution in ethanol and heated under refluxing for 3 hours. The reaction mixture was concentrated under reduced pressure and water was added to the concentrate. The mixture was extracted with chloroform and the extract was dried, followed by removal of the solvent by evaporation. The residue was submitted to silica gel column chromatography to obtain 4.24 gm of 1-(4-(1-benzylpiperidyl)methyl)-3,3-ethylenedioxy-2-pyrrolidone from a chloroform-methanol (25:1) fraction.

$^1$H-NMR δ ppm (CDCl$_3$) 7.34(s, 5H), 3.96(s, 4H), 3.57(s, 2H), 3.47(s,2H), 3.18(d, 2H), 2.93(b. d, 2H), 2.64(s, 2H), 2.2–1.2(m, 7H).

(3) 1-(4-(1-benzylpiperidyl)methyl)-3,3-ethylenedioxy-2-pyrrolidone (2.60 gm) was dissolved in 50 ml of methanol. To the solution was added 10 ml of 6N aqueous solution of hydrochloric acid, followed by heating under refluxing for 15 minutes. The reaction mixture was cooled, added to 100 ml of an ice-cooled 1N aqueous solution of sodium hydroxide, and extracted with ethyl acetate. The extract was washed with saturated brine and dried, followed by removal of the solvent by evaporation. The residue was submitted to silica gel column chromatography to obtain 1.30 gm of 1-(4-(1-benzylpiperidyl)methyl)-2,4-pyrrolidione from chloroform-methanol (50:1–20:1) fractions.

mp: 104°–105° C.

$^1$H-NMR δ ppm (CDCl$_3$): 7.34(s, 5H), 3.84(s, 2H), 3.77(s,2H), 3.55(s, 2H), 3.26(d, 2H), 2.92(b. d, 2H), 2.2–1.2(m, 7H).

IR ν neat$_{max}$ cm$^{-1}$: 1665, 1625.

Reference Example 3

The following compounds were prepared in the same manner as in Reference Example 2.

(1) N-(4-(1-benzylpiperidyl)ethyl)-4-chloro-3,3-ethylenedioxybutanamide $^1$H-NMR δ ppm (CDCl$_3$) 7.33(s, 5H), 6.05(br, 1H), 4.08(b. s, 4H), 3.61(s, 2H), 3.54(s, 2H), 3.29(m, 2H), 2.92(b. d, 2H), 2.70(s, 2H), 2.1–1.1(m, 9H).

(2) 1-(4-(1-benzylpiperidyl)ethyl)-3,3-ethylenedioxy-2-pyrrolidone $^1$H-NMR δ ppm (CDCl$_3$) 7.34(s, 5H), 3.97(s, 4H), 3.56(s, 2H), 3.45(s, 2H), 3.34(t, 2H), 2.92(b. d, 2H), 2.63(s, 2H), 2.2–1.1(m, 9H).

(3) 1-(4-(1-benzylpiperidyl)ethyl)-2,4-pyrrolidione $^1$H-NMR δ ppm (CDCl$_3$) 7.31(s, 5H), 3.79(s, 2H), 3.77(s, 2H), 3.50(s, 2H), 3.40(t, 2H), 2.88(b. d, 2H), 2.1–1.1(m, 9H).

IR ν neat$_{max}$ cm$^{-1}$: 1670, 1625.

Reference Example 4

9-Amino-1,2,3,4-tetrahydroacridin-1-one (10.6 gm) was suspended in 250 ml of acetonitrile, and to the suspension were added 16.4 gm of di-t-butyldicarbonate and 0.6 gm of 4-dimethylaminopyridine. After stirring for 5 hours at 50°–55° C., insoluble materials were removed by filtration, and the filtrate was evaporated under reduced pressure. The residue was submitted to silica gel column chromatography to obtain crystals from a chloroform-ethyl acetate (50:1) fraction. 11.0 gm of N-(1,2,3,4-tetrahydro-1-oxoacridin-9-yl) t-butylcarbamate was obtained by recrystallizing the crystals from petroleum ether.

mp: 127°–128° C.

$^1$H-NMR δ ppm (CDCl$_3$): 8.09(m, 2H), 7.86(m, 1H), 7.62(m, 1H), 3.36(t, 2H), 2.78(t, 2H), 2.26(m, 2H), 1.31(s, 9H).

Reference Example 5

The following compound was prepared in the same manner as in Reference Example 4.

N-(2,3-dihydro-1-oxocyclopenta[b]quinolin-9-yl) t-butylcarbamate $^1$H-NMR δ ppm (CDCl$_3$) 8.24–7.42(m, 4H), 3.45(m, 2H), 2.88(m, 2H), 1.35(s, 9H).

Reference Example 6

The following compounds were prepared in the same manner as in Reference Example 2.

(1) N-(4-(1-benzylpiperidyl)propyl)-4-chloro-3,3-ethylenedioxybutanamide $^1$H-NMR δ ppm (CDCl$_3$) 7.32(s, 5H), 6.10(br, 1H), 4.09(b. s, 4H), 3.61(s, 2H), 3.48(s, 2H), 3.22(m, 2H), 2.87(b. d, 2H), 2.70(s, 2H), 2.1–1.1(m, 11H).

(2) 1-(4-(1-benzylpiperidyl)propyl)-3,3-ethylenedioxy-2-pyrrolidone $^1$H-NMR δ ppm (CDCl$_3$) 7.35(s, 5H), 3.99(s, 4H), 3.54(s, 2H), 1.1(m, 11H).

(3) 1-(4-(1-benzylpiperidyl)propyl)-2,4-pyrrolidione mp: 71°–73° C.

$^1$H-NMR δ ppm (CDCl$_3$) 7.34(s, 5H), 3.81(s, 2H), 3.79(s, 2H), 3.51(s, 2H), 3.35(t, 2H), 2.89(b. d, 2H), 2.1–1.1(m, 9H).

IR ν KBr$_{max}$ cm$^{-1}$: 1675, 1625.

Example 1

1.32 gm of 1-(4-(1-benzylpiperidyl)methyl)-2,4-pyrrolidione and 0.58 gm of o-aminobenzonitrile were dissolved into 40 ml of benzene, and to the mixture 1.04 gm of p-toluenesulfonic acid monohydrate was added. The resulting mixture, placed in a reaction vessel equipped with a Dean-Stark water separator, was refluxed on an oil bath at 110°–120° C. for 9 hours while stirring. After cooling and an addition of 80 ml of 1N aqueous solution of sodium hydroxide, the mixture was extracted with chloroform. The extract was washed with saturated brine and dried, followed by removal of the solvent by evaporation under reduced pressure to obtain crystals, which were recrystallized in ethyl acetate to obtain 1.04 gm of N-(1-(4-(1-benzylpiperidyl)methyl)-2-oxo-3-pyrrolin-4-yl)-2-aminobenzonitrile (Compound (IIa) with R$^1$=R$^3$=H, n=1).

mp: 170°–171° C.

$^1$H-NMR δ ppm (CDCl$_3$) 7.75–7.02(m, 4H), 7.36(s, 5H), 6.95(b. s, 1H), 5.56(s, 1H), 4.14(s, 2H), 3.62(s, 2H), 3.32(d, 2H), 2.99(b. d, 2H), 2.3–1.2(m, 7H).

IR ν KBr$_{max}$ cm$^{-1}$: 2230, 1635, 1620.

The compounds of Examples 2 and 3 were prepared in the same manner as in Example 1.

Example 2

N-(1-(4-(1-benzylpiperidyl)ethyl)-2-oxo-3-pyrrolin-4-yl)-2-aminobenzonitrile (Compound (IIa) with R$^1$=R$^3$=H, n=2).

$^1$H-NMR δ ppm (CDC13) 7.73–7.03(m, 4H), 7.39(s, 5H), 6.82(b. s, 1H), 5,55(s, 1H), 4.09(s, 2H), 3.72(s, 2H), 3.45(t, 2H), 3.08(b. d, 2H), 2.4–1.2(m, 9H).

IR ν KBr$_{max}$ cm$^{-1}$: 2220, 1640, 1620.

Example 3

N-(1-(4-(1-benzylpiperidyl)propyl)-2-oxo-3-pyrrolin-4-yl)-2-aminobenzonitrile (Compound (IIa) with $R^1=R^3=H$, n=3).

$^1$H-NMR δ ppm (CDCl$_3$) 7.72-7.04(m, 2H), 7.36(s, 5H), 6.72(b. s, 1H), 5,60(s, 1H), 4.11(s, 2H), 3.56(s, 2H), 3.43(t, 2H), 2.93(b. d, 2H), 2.2–1.1(m, 11H).

IR ν KBr$_{max}$ cm$^{-1}$: 2220, 1650, 1620.

Example 4

N-(1-(4-(1-benzylpiperidyl)ethyl)-2-oxo-3-pyrrolin-4-yl)-2-aminobenzonitrile (0.19 gm) was dissolved in 1 ml of 2N HCl in methanol. After the addition of 0.06 gm of sodium cyanoborohydride, the mixture was stirred for 1 hour at room temperature. The reaction mixture was charged into 10 ml of 1N aqueous solution of sodium hydroxide and extracted with chloroform. The extract was dried and evaporated under reduced pressure. The residue was submitted to silica gel column chromatography to obtain 0.18 gm of N-(1-(4-(1-benzylpiperidyl)ethyl)-2-oxopyrrolidin-4-yl)-2-aminobenzonitrile (Compound (IIb) with $R^1=R^3=H$, n=2) from a chloroform-methanol (50:1) fraction.

$^1$H-NMR δ ppm (CDCl$_3$): 7.44(m, 2H), 7.31(s, 5H), 6.83(b. d, 1H), 6.63(b. d, 1H), 4.65(b. d, 1H), 4.24(m, 1H), 3.76(m, 2H), 3.50(s, 2H), 3.3(m, 4H), 3.0–1.1(m, 11H).

Example 5

The following compound was prepared in the same manner as in Example 4.

N-(1-(4-(1-benzylpiperidyl)propyl)-2-oxopyrrolidin-4-yl)-2-aminobenzonitrile (Compound (IIb) with $R^1=R^3=H$, n=3).

$^1$H-NMR δ ppm (CDCl$_3$) 7.45(m, 2H), 7.34(s, 5H), 6.84(b. d, 1H), 6.64(b. d, 1H), 4.66(b. d, 1H), 4.25(m, 1H), 3.81(m, 2H), 3,51(s, 2H), 3.31(m, 4H), 3.0–1.1(m, 13H).

Example 6

N-(1-(4-(1-benzylpiperidyl)methyl)-2-oxo-3-pyrrolin-4-yl)-2-aminobenzonitrile (0.84 gm) was dissolved into 40 ml of tetrahydrofuran, and to the solution were added 0.60 gm of potassium carbonate and 0.04 gm of copper (I) chloride. The mixture was refluxed for 8 hours while stirring. After removal of inorganic materials by filtration while the mixture was hot, the filtered cake was washed twice with 40 ml of hot tetrahydrofuran. The filtrate and washed liquid was combined and evaporated under reduced pressure. 0.58 gm of 9-amino-2-(4-(1-benzylpiperidyl)methyl)-2,3-dihydropyrrolo[3,4-b]quinolin-1-one (Compound (I) with $R^1=R^3=H$, $R^2=NH_2$, $A=>N-(CH_2)_n-$, $Y=>C=O$, m=1, and n=1) was obtained by recrystallizing the residue from ethyl acetate.

mp: 194°-195° C.

$^1$H-NMR δ ppm (CDCl$_3$) 7.95(m, 2H), 7.75(m, 1H), 7.49(m, 1H), 7.35(s, 5H), 6.50(br, 2H), 4.41(s, 2H), 3.62(s, 2H), 3.49(d, 2H), 2.99(b. d, 2H), 2.3–1.2(m, 7H).

IR ν KBr$_{max}$ cm$^{-1}$: 1675, 1640.

Example 7

The following compound was prepared in the same manner as in Example 6.

9-Amino-2-(4-(1-benzylpiperidyl)ethyl)-2,3-dihydropyrrolo-[3,4-b]quinolin-1-one (Compound (I) with $R^1=R^3=H$, $R^2=NH_2$, $A=>N-(CH_2)_n-$, $Y=>C=O$, m=1, and n=2).

mp: 178°-179° C.

$^1$H-NMR δ ppm (CDCl$_3$) 7.94(m, 2H), 7.73(m, 1H), 7,45(m, 1H), 7.32(s, 5H), 6.62(br, 2H), 4.36(s, 2H), 3.61(t, 2H), 3.52(s, 2H), 2.91(b. d, 2H), 2.1–1.2(m, 9H).

IR ν KBr$_{max}$ cm$^{-1}$: 1675, 1640.

Example 8

N-(1,2,3,4-tetrahydro-1-oxoacridin-9-yl) t-butylcarbamate (3.44 gm) was dissolved in 50 ml of dry tetrahydrofuran, and the solution was cooled to −78° C. in an argon atmosphere. To this were added dropwise 8 ml of 1.5M cyclohexane solution of lithium diisopropylamide and then 1.8 ml of hexamethylphosphoramide. After 15 minutes, 15 ml of dry tetrahydrofuran solution containing 2.38 gm of 1-benzyl-4-piperidine acetaldehyde was dropwise added. The mixture was stirred for 30 minutes at −78° C. and, after gradually raising its temperature to room temperature, for 3 hours. The resultant reaction mixture was charged into an ice-cooled 5% ammonium chloride aqueous solution and extracted with ethyl acetate. The extract was washed with saturated brine, dried, and evaporated under reduced pressure. The residue was submitted to silica gel column chromatography to obtain crystals from a chloroform-methanol (100:1–50:1) fractions. 2.60 gm of N-(2-(2-(1-benzylpiperidin-4-yl)ethylidene)-1,2,3,4-tetrahydro-1-oxoacridin-9-yl) t-butylcarbamate (Compound (I) with $R^1=R^3=H$, $R^2=-NHCOO-t-Bu$, $A=>C=CH(CH_2)_n-$, $Y=>C=O$, m=2, and n=1) was obtained by recrystallizing the crystals from ethanol.

mp: 116°-117° C.

$^1$H-NMR δ ppm (CDCl$_3$) 11.22(s, 1H), 8.00(m, 2H), 7.78(m, 1H), 7.50(m, 1H), 7.35(s, 5H), 7.09(t, 1H), 3.58(s, 2H), 3.3–1.2(m, 15H), 1.53(s,9H).

IR ν KBr$_{max}$ cm$^{-1}$: 1740, 1655.

The compounds of Examples 9–10 were prepared in the same manner as in Example 8.

Example 9

N-(2-(1-benzylpiperidin-4-yl)methylene-1,2,3,4-tetrahydro-1-oxoacridin-9-yl) t-butylcarbamate (Compound (I) with $R^1=R^3=H$, $R^2=-NHCOO-t-Bu$, $A=>C=CH(CH_2)_n-$, $Y=>C=O$, m=2, and n=0).

mp: 166°-167° C.

$^1$H-NMR δ ppm (CDCl$_3$): 11.15(s, 1H), 7.99(m, 2H), 7.78(m, 1H), 7.49(m, 1H), 7.39(s, 5H), 6.93(d, 1H), 3.70(s, 2H), 3.3–1.4(m, 13H), 1.53(s, 9H).

IR ν KBr$_{max}$ cm$^{-1}$: 1735, 1655.

Example 10

N-(2-(2-(1-benzylpiperidin-4-yl)ethylidene)-2,3-dihydro-1-oxocyclopenta[b]quinolin-9-yl) t-butylcarbamate (Compound (I) with $R^1=R^3=H$, $R^2=-NHCOO-t-Bu$, $A=>C=CH(CH_2)_n-$, $Y=>C=O$, m=1, and n=1).

mp: 152°-153° C.

$^1$H-NMR δ ppm (CDCl$_3$) 9.83(b. s, 1H), 8.30(b. d, 1H), 8.07(b. d, 1H), 7.83(m, 1H), 7.53(m, 1H), 7.38(b. s, 5H), 6.97(b. t, 1H), 3.80(b. s, 2H), 3.67(s, 2H), 3.04(b. d, 2H), 2.4–1.4(m, 9H), 1.54(s, 9H).

IR ν KBr$_{max}$ cm$^{-1}$: 1745, 1705.

Example 11

N-(2-(2-(1-benzylpiperidin-4-yl)ethylidene)-1,2,3,4-tetrahydro-1-oxoacridin-9-yl) t-butylcarbamate (1.08 gm) was dissolved in 20 ml of tetrahydrofuran, and to the solution was added 0.20 gm of 10% palladium-carbon. The mixture was hydrogenated for 10 hours at room temperature under normal pressure. After removal of palladium-carbon by filtration, the filtrate was evaporated under reduced pressure. The residue was submitted to silica gel column chromatography to obtain 1.02 gm of N-(2-(2-(1-benzylpiperidin-4-yl)ethyl)-1,2,3,4-tetrahydro-1-oxoacridin-9-yl) t-butylcarbamate (Compound (I) with $R^1=R^3=H$, $R^2=$—NHCOO—t—Bu, $A=>CH(CH_2)_n$—, $Y=>C=O$, $m=2$, and $n=2$) was obtained from a chloroform-methanol (50:1) fraction.

mp: 92°–94° C.

$^1$H-NMR δ ppm (CDCl$_3$) 11.06(s, 1H), 7.98(m, 2H), 7.77(m, 1H), 7.48(m, 1H), 7.35(s, 5H), 3.57(s, 2H), 3.4–1.2(m, 18H), 1.52(s, 9H).

IR ν KBr$_{max}$ cm$^{-1}$: 1740, 1650.

The compounds of Examples 12 and 13 were prepared in the same manner as in Example 11.

Example 12

N-(2-(1-benzylpiperidin-4-yl)methyl)-1,2,3,4-tetrahydro-1-oxoacridin-9-yl) t-butylcarbamate (Compound (I) with $R^1=R^3=H$, $R^2=$—NHCOO—t—Bu, $A=>CH(CH_2)_n$—, $Y=>C=O$, $m=2$, and $n=1$).

$^1$H-NMR δ ppm (CDCl$_3$) 11.01(s, 1H), 7.98(m, 2H), 7.78(m, 1H), 7.48(m, 1H), 7.39(b. s, 5H), 3.68(s, 2H), 3.4–1.2(m, 16H), 1.52(s, 9H).

IR ν KBr$_{max}$ cm$^{-1}$: 1735, 1645.

Example 13

N-(2-(2-(1-benzylpiperidin-4-yl)ethyl)-2,3-dihydro-1-oxocyclopenta[b]quinolin-9-yl) t-butylcarbamate (Compound (I) with $R^1=R^3=H$, $R^2=$—NHCOO—t—Bu, $A=>CH(CH_2)_n$—, $Y=>C=O$, $m=2$, and $n=2$).

mp: 141°–143° C.

$^1$H-NMR δ ppm (CDCl$_3$) 9.63(b. s, 1H), 8.29(b. d, 1H), 8.06(b. d, 1H), 7.83(m, 1H), 7.53(m, 1H), 7.38(b. s, 5H), 3.67(s, 2H), 3.4–1.2(m, 16H), 1.55(s, 9H).

IR ν KBr$_{max}$ cm$^{-1}$: 1745, 1670.

Example 14

N-(2-(2-(1-benzylpiperidin-4-yl)ethyl)-1,2,3,4-tetrahydro-1-oxoacridin-9-yl) t-butylcarbamate (0.5 gm) was dissolved in 5 ml of dioxane, and to the solution was added 15 ml of 4N dioxane solution of hydrochloric acid, followed by stirring for 8 hours at room temperature. After evaporation under reduced pressure, acetone was added to the residue to produce a powdery material. The powder was collected by filtration, and dried to obtain 0.48 gm of 9-amino-2-(2-(1-benzylpiperidin-4-yl)ethyl)-1,2,3,4-tetrahydroacridin-1-one dihydrochloride (Compound (I) with $R^1=R^3=H$, $R^2=NH_2$, $A=>CH(CH2)_n$—, $Y=>C=O$, $m=2$, and $n=2$).

$^1$H-NMR δ ppm (DMSO-d$_6$) 8.75(b. d, 1H), 8.14(m, 1H), 8.00(m, 1H), 7.70(m, 3H), 7.44(m, 3H), 4.22(b. s, 2H), 3.7–2.6(m, 7H), 2.4–1.2(m, 11H).

IR ν KBr$_{max}$ cm$^{-1}$: 1630.

The compounds in Examples 14–18 were prepared in the same manner as in Example 14.

Example 15

9-Amino-2-(1-benzylpiperidin-4-yl)methyl)-1,2,3,4-tetrahydroacridin-1-one dihydrochloride (Compound (I) with $R^1=R^3=H$, $R^2=NH_2$, $A=>CH(CH_2)_n$—, $Y=>C=O$, $m=2$, and $n=1$).

$^1$H-NMR δ ppm (DMSO-d$_6$) 8.76(b. d, 1H), 8.15(m, 1H), 8.00(m, 1H), 7.69(m, 3H), 7.45(m, 3H), 4.21(b. s, 2H), 3.9–2.6(m, 7H), 2.4–1.4(m, 9H).

IR ν KBr$_{max}$ cm$^{-1}$: 1630.

Example 16

9-Amino-2-(2-(1-benzylpiperidin-4-yl)ethyl)-2,3-dihydrocyclopenta[b]quinolin-1-one dihydrochloride (Compound (I) with $R^1=R^3=H$, $R^2=NH_2$, $A=>CH(CH_2)_n$—, $Y=>C=O$, $m=1$, and $n=2$).

mp: 218°–220° C.

$^1$H-NMR δ ppm (CD$_3$OD): 8.56(b. d, 1H), 8.18–7.58(m, 3H), 7.53(b. s, 5H), 4.30(b. s, 2H), 3.6–2.7(m, 7H), 2.2–1.3(m, 9H).

IR ν KBr$_{max}$ cm$^{-1}$: 1690, 1640.

Example 17

9-Amino-2-(2-(1-benzylpiperidin-4-yl)ethylidene)-1,2,3,4-tetrahydroacridin-1-one dihydrochloride (Compound (I) with $R^1=R^3=H$, $R^2=NH_2$, $A=>C=CH(CH_2)_n$—, $Y=>C=O$, $m=2$, and $n=1$).

mp: 208°–210° C.

$^1$H-NMR δ ppm (DMSO-d$_6$) 8.76(b. d, 1H), 8.14(m, 1H), 7.99(m, 1H), 7.69(m, 3H), 7.42(m, 3H), 6.85(b. t, 1H), 4.21(b. s, 2H), 3.6–2.6(m, 10H), 2.4–1.6(m, 5H).

IR ν KBr$_{max}$ cm$^{-1}$: 1630.

Example 18

9-Amino-2-(1-benzylpiperidin-4-yl)methylene)-1,2,3,4-tetrahydroacridin-1-one dihydrochloride (Compound (I) with $R^1=R^3=H$, $R^2=NH_2$, $A=>C=CH(CH_2)_n$—, $Y=>C=O$, $m=2$, and $n=0$).

mp: 230°–232° C.

$^1$H-NMR δ ppm (DMSO-d$_6$) 8.77(b. d, 1H), 8.18(m, 1H), 8.02(m, 1H), 7.72(m, 3H), 7.46(m, 3H), 6.60(b. d, 1H), 4.27(b. s, 1H), 3.5–2.6(m, 9H), 2.4–1.6(m, 4H).

IR ν KBr$_{max}$ cm$^{-1}$: 1630.

Example 19

The following compound was prepared in the same manner as in Example 6.

9-Amino-2-(4-(1-benzylpiperidyl)propyl)-2,3-dihydropyrrolo[3,4-b]quinolin-1-one (Compound (I) with $R^1=R^3=H$, $R^2=NH_2$, $A=>N$—$(CH_2)_n$—, $Y=>C=O$, $m=1$, and $n=3$).

mp: 155°–157° C.

$^1$H-NMR δ ppm (CDCl$_3$): 7.93(m, 2H), 7.71(m, 1H), 7.49(m, 1H), 7.36(s, 5H), 6.59(br, 2H), 4.41(b. s, 2H), 3.59(t, 2H), 3.52(s, 2H), 2.91(b. d, 2H), 2.2–1.1(m, 11H).

IR ν KBr$_{max}$ cm$^{-1}$: 1675, 1640.

Reference Example 7

The following compound was prepared in the same manner as in Reference Example 4.

N-(8-fluoro-1,2,3,4-tetrahydro-1-oxoacridin-9-yl) t-butylcarbamate.

mp: 108°–110° C.

$^1$H-NMR δ ppm (CDCl$_3$): 7.77(m, 2H), 7.22(m, 1H), 3.30(t, 2H), 2.76(t, 2H), 2.20(m, 2H), 1.35(s, 9H).

IR ν KBr$_{max}$ cm$^{-1}$: 1755, 1710.

Reference Example 8

The following compound was prepared in the same manner as in Reference Example 4.

N-(8-fluoro-1,2,3,4-tetrahydro-1-oxoacridin-9-yl) t-butylcarbamate.

mp: 204°–205° C.

$^1$H-NMR δ ppm (CDCl$_3$) 8.20-7.50(m, 4H), 3.21(t, 2H), 2.72(b.t, 2H), 1.94(m, 4H), 1.34(s, 9H).
IR ν KBr$_{max}$ cm$^{-1}$: 1720, 1690.

Reference Example 9

15.1 gm of methyl anthranilate and 9.0 gm of β-tetronic acid were dissolved into 100 ml of ethanol, and 2 ml of concentrated hydrochloric acid was added, followed by stirring for 15 hours at room temperature. Deposited crystals were collected by filtration, washed with cold ethanol, and dried to obtain 19.2 gm of methyl N-(2,5-dihydro-5-oxo-2-furanyl)anthranilate.
mp: 172°-173° C.
$^1$H-NMR δ ppm (DMSO-d$_6$): 9.95(b.s, 1H), 7.97(d.d, 1H), 7.59(m, 2H), 7.20(m, 1H), 5.40(s, 1H), 4.94(s, 2H), 3.86(s, 3H).
IR ν KBr$_{max}$ cm$^{-1}$: 1735.

The compounds of Reference Examples 10-16 were prepared in the same manner as in Reference Example 9.

Reference Example 10

Methyl N-(2,5-dihydro-5-oxo-2-furanyl)-6-methylthioanthranilate.
$^1$H-NMR δ ppm (CDCl$_3$) 9.08(b.s, 1H), 7.47(t, 1H), 7.21(d.d, 1H), 7.05(d, 1H), 5.38(s, 1H), 4.84(s, 2H), 3.97(s, 3H), 2.45(s, 3H).

Reference Example 11

N-(2,5-dihydro-5-oxo-2-furanyl)-4-chloroanthranilic acid.
mp: 211°-212° C.
$^1$H-NMR δ ppm (DMSO-d$_6$) 10.30(br, 1H), 8.00(d, 1H), 7.49(d, 1H), 7.22(d.d, 1H), 5.51(s, 1H), 4.95(s, 2H).
IR ν KBr$_{max}$ cm$^{-1}$: 1720, 1680.

Reference Example 12

N-(2,5-dihydro-5-oxo-2-furanyl)-5-chloroanthranilic acid.
mp: 248°-250° C.
$^1$H-NMR δ ppm (DMSO-d$_6$): 10.16(br, 1H), 7.96(d, 1H), 7.68(d.d, 1H), 7.55(d, 1H), 5.47(s, 2H), 4.94(s, 2H).
IR ν KBr$_{max}$ cm$^{-1}$: 1720, 1680.

Reference Example 13

N-(2,5-dihydro-5-oxo-2-furanyl)-2-aminobenzonitrile.
mp: 158°-160° C.
$^1$H-NMR δ ppm (DMSO-d$_6$): 9.68(br, 1H), 7.80(d.d, 1H), 7.69(d.d, 1H), 7.60(m, 1H), 7.32(m, 1H), 5.10(s, 1H), 4.86(s, 2H).
IR ν KBr$_{max}$ cm$^{-1}$: 2230, 1730.

Reference Example 14

N-(2,5-dihydro-5-oxo-2-furanyl)-2-amino-6-fluorobenzonitrile.
mp: 234°-235° C.
$^1$H-NMR δ ppm (DMSO-d$_6$) 9.86(br, 1H), 7.76(m, 1H), 7.41(d, 1H), 7.21(t, 1H), 5.26(s, 1H), 4.88(s, 2H).
IR ν KBr$_{max}$ cm$^{-1}$: 2230, 1735.

Reference Example 15

N-(2,5-dihydro-5-oxo-2-furanyl)-2-amino-6-methylthiobenzonitrile.
mp: 180°-182° C.
$^1$H-NMR δ ppm (DMSO-d$_6$)·9.76(b.s, 1H), 7.66(t, 1H), 7.32(d, 1H), 7.24(d, 1H), 5.11(s, 1H), 4.87(s, 2H), 2.57(s, 3H).

Reference Example 16

N-(2,5-dihydro-5-oxo-2-furanyl)-2-amino-6-methoxybenzonitrile.
mp: 178°-180° C.
$^1$H-NMR δ ppm (DMSO-d$_6$) 9.70(br, 1H), 7.66(t, 1H), 7.12(d, 1H), 7.01(d, 1H), 5.14(s, 1H), 4.87(s, 2H), 3.92(s, 3H).
IR ν KBr$_{max}$ cm$^{-1}$: 2210, 1735.

Reference Example 17

To 4.66 gm of methyl N-(2,5-dihydro-5-oxo-2-furanyl)anthranilate was added 13.6 gm of polyphosphoric acid, and the mixture was heated for 3 hours at 130°-140° C. on an oil bath while stirring. After cooling, 100 ml of water was added and the mixture was stirred for 1 hour to collect the deposited crystals by filtration. The crystals were washed with water and recrystallized from methanol to obtain 3.50 gm of 9-hydroxyfuro[3,4-b]quinolin-1(3H)-one.
mp: 280° C. (decomposed).
$^1$H-NMR δ ppm (DMSO-d$_6$) 12.68(br, 1H), 8.25(d, 1H), 7.90-7.35(m, 3H), 5.23(s, 2H).
IR ν KBr$_{max}$ cm$^{-1}$: 1740.

The compounds of Reference Examples 18-20 were prepared in the same manner as in Reference Example 17.

Reference Example 18

9-Hydroxy-8-methylthiofuro[3,4-b]quinolin-1(3H)-one.
mp: 220° C. (decomposed).
$^1$H-NMR δ ppm(CD$_3$OD): 7.87(m, 2H), 7.22(m, 1H), 5.09(s, 2H), 2.47(s, 3H).
IR ν KBr$_{max}$ cm$^{-1}$: 1770.

Reference Example 19

6-Chloro-9-hydroxyfuro[3,4-b]quinolin-1(3H)-one.
mp: 270° C. (decomposed).
$^1$H-NMR δ ppm (DMSO-d$_6$): 8.24(d, 1H), 7.68(d, 1H), 7.50(d.d, 1H), 5.27(s, 2H).
IR ν KBr$_{max}$ cm$^{-1}$: 1745.

Reference Example 20

7-Chloro-9-hydroxyfuro[3,4-b]quinolin-1(3H)-one.
mp: >300° C.
$^1$H-NMR δ ppm (DMSO-d$_6$) 8.15(d, 1H), 7.82(d.d, 1H), 7.66(d, 1H), 5.26(s, 2H).
IR ν KBr$_{max}$ cm$^{-1}$: 1750.

Reference Example 21

6.00 gm of N-(2,5-dihydro-5-oxo-2-furanyl)-2-aminobenzonitrile was suspended in 300 ml of 1,4-dioxane. To the suspension were added 8.28 gm of potassium carbonate and 0.20 gm of copper (I) chloride, and the mixture was refluxed for 10 hours while stirring. After removal inorganic materials by filtration while the mixture was hot, the filtered cake was washed twice with 300 ml of hot 1,4-dioxane. The filtrate and washed liquid was combined and evaporated under reduced pressure. The residue was recrystallized from acetone to obtain 2.80 gm of 9-aminofuro[3,4-b]quinolin-1(3H)-one.
mp 190°-192° C.
$^1$H-NMR δ ppm (DMSO-d$_6$): 8.44(d, 1H), 7.83(m, 4H), 7.48(m, 1H), 5.22(s, 2H).
IR ν KBr$_{max}$ cm$^{-1}$: 1720.

The compounds of Reference Examples 22-24 were prepared in the same manner as in Reference Example 21.

Reference Example 22

9-Amino-8-methylthiofuro[3,4-b]quinolin-1(3H)-one.
$^1$H-NMR δ ppm (CDCl$_3$): 7.93(t, 1H), 7.66(d, 2H), 5.24(s, 2H), 2.56(s, 3H).
IR ν KBr$_{max}$ cm$^{-1}$: 1710.

Reference Example 23

9-Amino-8-fluorofuro[3,4-b]quinolin-1(3H)-one.
$^1$H-NMR δ ppm (CDCl$_3$) 7.68(m, 2H), 7.06(m, 1H), 7.4-6.6(br, 2H), 5.20(s, 2H).
IR ν KBr$_{max}$ cm$^{-1}$: 1735.

Reference Example 24

9-Amino-8-methoxyfuro[3,4-b]quinolin-1(3H)-one.
$^1$H-NMR δ ppm (CDCl$_3$) 7.59(m, 2H), 7.8-7.2(br, 2H), 6.86(d, 1H), 5.21(s, 2H), 4.05(s, 3H).
IR ν KBr$_{max}$ cm$^{-1}$: 1715.

The compounds of Examples 20-31 were prepared in the same manner as in Example 8.

Example 20

N-(2-(3-(1-benzylpiperidin-4-yl)propylidene)-1,2,3,4-tetrahydro-1-oxoacridin-9-yl) t-butylcarbamate (Compound (I) with R$^1$=R$^3$=H, R$^2$=—NHCOO—t—Bu, A=>C=CH(CH$_2$)$_n$—, Y=>C=O, m=2, and n=2).
mp: 120°-122° C.
$^1$H-NMR δ ppm (CDCl$_3$) 11.24(s, 1H), 8.00(m, 2H), 7.79(m, 1H), 7.50(m, 1H), 7.34(s, 5H), 7.08(t, 1H), 3.52(s, 2H), 3.3-1.1(m, 17H), 1.53(s, 9H).
IR ν KBr$_{max}$ cm$^{-1}$: 1735, 1655.

Example 21

N-(2-(4-(1-benzylpiperidin-4-yl)butylidene)-1,2,3,4-tetrahydro-1-oxoacridin-9-yl) t-butylcarbamate (Compound (I) with R$^1$=R$^3$=H, R$^2$=—NHCOO—t—Bu, A=>C=CH(CH$_2$)$_n$—, Y=>C=O, m=2, and n=3).
mp: 115°-117° C.
$^1$H-NMR δ ppm (CDCl$_3$) 11.22(s, 1H), 8.00(m, 2H), 7.78(m, 1H), 7.51(m, 1H), 7.33(s, 5H), 7.09(t, 1H), 3.50(s, 2H), 3.3-1.1(m, 19H), 1.53(s, 9H).
IR ν KBr$_{max}$ cm$^{-1}$: 1735, 1655.

Example 22

N-(2-(1-benzylpiperidin-4-ylidene)-1,2,3,4-tetrahydro-1-oxoacridin-9-yl) t-butylcarbamate (Compound (I) with R$^1$=R$^3$=H, R$^2$=—NHCOO—t—Bu, A=>C=, Y=>C=O, and m=2).
mp: 113°-115° C.
$^1$H-NMR δ ppm (CDCl$_3$) 11.14(s, 1H), 7.99(m, 2H), 7.77(m, 1H), 7.48(m, 1H), 7.37(s, 5H), 3.61(s, 2H), 3.3-2.5(m, 12H), 1.53(s, 9H).
IR ν KBr$_{max}$ cm$^{-1}$: 1730, 1650.

Example 23

N-(2-(6-(1-benzylpiperidin-4-yl)hexylidene)-1,2,3,4-tetrahydro-1-oxoacridin-9-yl) t-butylcarbamate (Compound (I) with R$^1$=R$^3$=H, R$^2$=—NHCOO—t—Bu, A=>C=CH(CH$_2$)$_n$—, Y=>C=O, m=2, and n=5).
$^1$H-NMR δ ppm (CDCl$_3$) 11.24(s, 1H), 8.00(m, 2H), 7.79(m, 1H), 7.50(m, 1H), 7.33(s, 5H), 7.09(t, 1H), 3.51(s, 2H), 3.3-1.1(m, 23H), 1.53(s, 9H).
IR ν KBr$_{max}$ cm$^{-1}$: 1740, 1655.

Example 24

N-(2-(2-(1-benzylpiperidin-4-yl)ethylidene)-8-fluoro-1,2,3,4-tetrahydro-1-oxoacridin-9-yl) t-butylcarbamate (Compound (I) with R$^1$=8—F, R$^2$=—NHCOO—t—Bu, R$^3$=H, A=>C=CH(CH$_2$)$_n$—, Y=>C=O, m=2, and n=1).
mp: 138°-140° C.
$^1$H-NMR δ ppm (CDCl$_3$): 11.20(s, 1H), 7.74(m, 2H), 7.36(s, 5H), 7.34(m, 1H), 7.09(t, 1H), 3.56(s, 2H), 3.3-1.2(m, 15H), 1.51(s, 9H).
IR ν KBr$_{max}$ cm$^{-1}$: 1745, 1660.

Example 25

N-(2-(4-(1-benzylpiperidin-4-yl)butylidene)-8-fluoro-1,2,3,4-tetrahydro-1-oxoacridin-9-yl) t-butylcarbamate (Compound (I) with R$^1$=8—F, R$^2$=—NHCOO—t—Bu, R$^3$=H, A=>C=CH(CH$_2$)$_n$—, Y=>C=O, m=2, and n=3).
$^1$H-NMR δ ppm (CDCl$_3$): 11.22(s, 1H), 7.74(m, 2H), 7.35(s, 5H), 7.32(m, 1H), 7.08(t, 1H), 3.56(s, 2H), 3.3-1.1(m, 19H), 1.51(s, 9H).
IR ν KBr$_{max}$ cm$^{-1}$: 1740, 1660.

Example 26

N-(2-(2-(1-benzylpiperidin-4-yl)ethylidene)-2,3,4,5-tetrahydro-1-oxocyclohepta[b]quinolin-11-yl) t-butylcarbamate (Compound (I) with R$^1$=R$^3$=H, R$^2$=—NHCOO—t—Bu, A=>C=CH(CH$_2$)$_n$—, Y=>C=O, m=3, and n=1).
mp: 188°-189° C.
$^1$H-NMR δ ppm (CDCl$_3$) 8.73(s, 1H), 8.01(m, 2H), 7.76(m, 1H), 7.53(m, 1H), 7.33(s, 5H), 7.07(t, 1H), 3.53(s, 2H), 3.1-1.2(m, 17H), 1.47(s, 9H).
IR ν KBr$_{max}$ cm$^{-1}$: 1715, 1670.

Example 27

9-Methylamino-2-(2-(1-benzylpiperidin-4-yl)ethylidene)-1,2,3,4-tetrahydroacridin-1-one (Compound (I) with R$^1$=R$^3$=H, R$^2$=—NHCH$_3$, A=>C=CH(CH$_2$)$_n$—, Y=>C=O, m=2, and n=1).
mp: 114°-116° C.
$^1$H-NMR δ ppm (CDCl$_3$) 11.40(br, 1H), 8.38(d, 1H), 7.84(m, 1H), 7.70(m, 1H), 7.38(m, 1H), 7.34(s, 5H), 6.94(t, 1H), 3.57(d, 3H), 3.52(s, 3H), 3.2-1.2(m, 15H).
IR ν KBr$_{max}$ cm$^{-1}$: 1625.

Example 28

9-Ethylamino-2-(2-(1-benzylpiperidin-4-yl)ethylidene)-1,2,3,4-tetrahydroacridin-1-one (Compound (I) with R$^1$=R$^3$=H, R$^2$=—NHC$_2$H$_5$, A=>C=CH(CH$_2$)$_n$—, Y=>C=O, m=2, and n=1).
$^1$H-NMR δ ppm (CDCl$_3$): 11.50(br, 1H), 8.27(d, 1H), 7.80(m, 1H), 7.66(m, 1H), 7.31(m, 1H), 7.29(s, 5H), 6.91(t, 1H), 3.94(m, 2H), 3.47(s, 2H), 3.2-1.2(m, 15H), 1.45(t, 3H).
IR ν KBr$_{max}$ cm$^{-1}$: 1630.

Example 29

9-Benzylamino-2-(2-(1-benzylpiperidin-4-yl)ethylidene)-1,2,3,4-tetrahydroacridin-1-one (Compound (I) with R$^1$=R$^3$=H, 1H), 7.66(m, 1H), 7.42(s, 5H), 7.3(m, 1H), 7.30(s, 5H), 5.06(d, 1H), 3.47(s, 2H), 3.2-1.2(m, 15H).
IR ν KBr$_{max}$ cm$^{-1}$: 1630.

Example 30

9-Methylamino-2-(2-(1-benzylpiperidin-4-yl]ethylidene)-2,3,-dihydrocyclopenta[b]quinolin-1-one (Compound (I) with $R^1=R^3=H$, $R^2=-NHCH_3$, $A=>C=CH(CH_2)_n-$, $Y=>C=O$, $m=1$, and $n=1$).

$^1$H-NMR $\delta$ ppm (CDCl$_3$) 9.41(br, 1H), 8.43(d, 1H), 7.95(d.d, 1H), 7.72(m, 1H), 7.37(m, 1H), 7.31(s, 5H), 6.80(t, 1H), 3.61(s, 2H), 3.57(d, 3H), 3.49(s, 2H), 2.89(b.d, 2H), 2.3–1.2(m, 9H).

IR $\nu$ KBr$_{max}$ cm$^{-1}$: 1675.

Example 31

N-(2-(2-(1-benzylpiperidin-4-yl)ethylidene)-1,2,3,4-tetrahydro-1-oxoacridin-9-yl) acetamide (Compound (I) with $R^1=R^3=H$, $R^2=-NHCOCH_3$, $A=>C=CH(CH_2)_n-$, $Y=>C=O$, $m=2$, and $n=1$).

$^1$H-NMR $\delta$ ppm (CDCl$_3$): 11.62(s, 1H), 7.98(m, 2H), 7.79(m, 1H), 7.50(m, 1H), 7.34(s, 5H), 7.09(t, 1H), 3.59(s, 2H), 3.3–1.2(m, 15H), 2.38(s, 3H).

IR $\nu$ KBr$_{max}$ cm$^{-1}$: 1680, 1650.

The compounds of Examples 32–42 were prepared in the same manner as in Example 11.

Example 32

N-(2-(3-(1-benzylpiperidin-4-yl)propyl)-1,2,3,4-tetrahydro-1-oxoacridin-9-yl) t-butylcarbamate (Compound (I) with $R^1=R^3=H$, $R^2=-NHCOO-t-Bu$, $A=>CH(CH_2)_n-$, $Y=>C=O$, $m=2$, and $n=3$).

$^1$H-NMR $\delta$ ppm (CDCl$_3$) 11.08(s, 1H), 7.98(m, 2H), 7.78(m, 1H), 7.48(m, 1H), 7.33(s, 5H), 3.52(s, 2H), 3.4–1.1(m, 20H), 1.52(s, 9H).

IR $\nu$ KBr$_{max}$ cm$^{-1}$: 1740, 1650.

Example 33

N-(2-(4-(1-benzylpiperidin-4-yl)butyl)-1,2,3,4-tetrahydro-1-oxoacridin-9-yl) t-butylcarbamate (Compound (I) with $R^1=R^3=H$, $R^2=-NHCOO-t-Bu$, $A=>CH(CH_2)_n-$, $Y=>C=O$, $m=2$, and $n=4$).

mp: 108°–110° C.

$^1$H-NMR $\delta$ ppm (CDCl$_3$): 11.12(s, 1H), 7.99(m, 2H), 7.77(m, 1H), 7.48(m, 1H), 7.33(s, 5H), 3.50(s, 2H), 3.41–1.1(m, 22H), 1.53(s, 9H).

IR $\nu$ KBr$_{max}$ cm$^{-1}$: 1740, 1650.

Example 34

N-(2-(6-(1-benzylpiperidin-4-yl)hexyl)-1,2,3,4-tetrahydro-1-oxoacridin-9-yl) t-butylcarbamate (Compound (I) with $R^1=R^3=H$, $R^2=-NHCOO-t-Bu$, $A=>CH(CH_2)_n-$, $Y=>C=O$, $m=2$, and $n=6$).

$^1$H-NMR $\delta$ ppm (CDCl$_3$) 11.12(s, 1H), 7.98(m, 2H), 7.77(m, 1H), 7.48(m, 1H), 7.34(s, 5H), 3.56(s, 2H), 3.3–1.0(m, 26H), 1.52(s, 9H).

IR $\nu$ KBr$_{max}$ cm$^{-1}$: 1735, 1650.

Example 35

N-(2-(2-(1-benzylpiperidin-4-yl)ethyl)-8-fluoro-1,2,3,4-tetrahydro-1-oxoacridin-9-yl) t-butylcarbamate (Compound (I) with $R^1=8-F$, $R^2=-NHCOO-t-Bu$, $R^3=H$, $A=>CH(CH_2)_n-$, $Y=>C=O$, $m=2$, and $n=2$).

$^1$H-NMR $\delta$ ppm (CDCl$_3$) 11.14(s, 1H), 7.72(m, 2H), 7.33(s, 5H), 7.3(m, 1H), 3.52(s, 2H), 3.3–1.1(m, 18H), 1.50(s, 9H).

IR $\nu$ KBr$_{max}$ cm$^{-1}$: 1745, 1650.

Example 36

9-Amino-2-(4-(1-benzylpiperidin-4-yl)butyl)-8-fluoro-1,2,3,4-tetrahydroacridin-1-one dihydrochloride (Compound (I) with $R^1=8-F$, $R^2=-NH_2$, $R^3=H$, $A=>CH(CH_2)_n-$, $Y=>C=O$, $m=2$, and $n=4$).

$^1$H-NMR $\delta$ ppm (DMSO-d$_6$) 7.99(m, 2H), 7.64(m, 3H), 7.44(m, 3H), 4.21(b. s, 2H), 3.5–2.6(m, 7H), 2.4–1.2(m, 15H).

IR $\nu$ KBr$_{max}$ cm$^{-1}$: 1635.

Example 37

11-Amino-2-(2-(1-benzylpiperidin-4-yl)ethyl)-2,3,4,5-tetrahydrocyclohepta[b]quinolin-1-one (Compound (I) with $R^1=R^3=H$, $R^2=-NH_2$, $A=>CH(CH_2)_n-$, $Y=>C=O$, $m=3$, and $n=2$).

mp: 73°–75° C.

$^1$H-NMR $\delta$ ppm (CDCl$_3$) 7.88(m, 2H), 7.71(m, 1H), 7.43(m, 1H), 7.33(s, 5H), 3.53(s, 2H), 3.4–2.7(m, 5H), 2.4–1.1(m, 15H).

IR $\nu$ KBr$_{max}$ cm$^{-1}$: 1630.

Example 38

9-Methylamino-2-(2-(1-benzylpiperidin-4-yl)ethyl)-1,2,3,4-tetrahydroacridin-1-one (Compound (I) with $R^1=R^3=H$, $R^2=NHCH_3$, $A=>CH(CH_2)_n-$, $Y=>C=O$, $m=2$, and $n=2$).

$^1$H-NMR $\delta$ ppm (CDCl$_3$) 11.40(br, 1H), 8.37(d, 1H), 7.85(m, 1H), 7.69(m, 1H), 7.35(s, 5H), 7.3(m, 1H), 3.57(s, 2H), 3.52(d, 3H), 3.2–2.5(m, 5H), 2.5–1.1(m, 13H).

IR $\nu$ KBr$_{max}$ cm$^{-1}$: 1620.

Example 39

9-Ethylamino-2-(2-(1-benzylpiperidin-4-yl)ethyl)-1,2,3,4-tetrahydroacridin-1-one (Compound (I) with $R^1=R^3=H$, $R^2=NHC_2H_5$, $A=>CH(CH_2)_n-$, $Y=>C=O$, $m=2$, and $n=2$).

$^1$H-NMR $\delta$ ppm (CDCl$_3$) 11.52(br, 1H), 8.26(d, 1H), 7.78(m, 1H), 7.65(m, 1H), 7.32(s, 5H), 7.3(m, 1H), 3.93(m, 2H), 3.49(s, 2H), 3.2–2.6(m, 5H), 1.45(t, 3H), 2.3–1.2(m, 13H).

IR $\nu$ KBr$_{max}$ cm$^{-1}$: 1620.

Example 40

9-Benzylamino-2-(2-(1-benzylpiperidin-4-yl)ethyl)-1,2,3,4-tetrahydroacridin-1-one (Compound (I) with $R^1=R^3=H$, $R^2=NHCH_2Ph$, $A=>CH(CH_2)_n-$, $Y=>C=O$, $m=2$, and $n=2$).

$^1$H-NMR $\delta$ ppm (CDCl$_3$) 11.70(br, 1H), 8.16(d, 1H), 7.80(m, 1H), 7.64(m, 1H), 7.39(s, 5H), 7.3(m, 1H), 7.29(s, 5H), 5.02(d, 2H), 3.47(s, 2H), 3.2–2.7(m, 5H), 2.6–1.1(m, 13H).

IR $\nu$ KBr$_{max}$ cm$^{-1}$: 1630.

Example 41

9-Methylamino-2-(2-(1-benzylpiperidin-4-yl)ethyl)-2,3-dihydrocyclopenta[b]quinolin-1-one (Compound (I) with $R^1=R^3=H$, $R^2=NHCH_3$, $A=>CH(CH_2)_n-$, $Y=>C=O$, $m=1$, and $n=2$).

$^1$H-NMR $\delta$ ppm (CDCl$_3$): 9.25(br, 1H), 8.41(d, 1H), 7.89(d. d, 1H), 7.71(m, 1H), 7.36(m, 1H), 7.31(s, 5H), 3.55(d, 3H), 3.50(s, 2H), 3.5–2.6(m, 5H), 2.1–1.1(m, 11H).

IR $\nu$ KBr$_{max}$ cm$^{-1}$: 1670.

Example 42

N-(2-(2-(1-benzylpiperidin-4-yl)ethyl)-1,2,3,4-tetrahydro-1-oxoacridin-9-yl) acetamide (Compound (I)

with R¹=R³=H, R²=NHCOCH₃, A=>CH(CH₂)ₙ—, Y=>C=O, m=2, and n=2).

mp: 150°-152° C.

¹H-NMR δ ppm (CDCl₃) 11.49(s, 1H), 7.95(m, 2H), 7.78(m, 1H), 7.48(m, 1H), 7.34(s, 1H), 3.55(s, 2H), 3.4-2.8(m, 5H), 2.38(s, 3H), 2.5-1.1(m, 13H).

IR ν KBr$_{max}$ cm⁻¹: 1680, 1650.

The compounds of Examples 43-53 were prepared in the same manner as in Example 14.

Example 43

9-Amino-2-(3-(1-benzylpiperidin-4-yl)propylidene)-1,2,3,4-tetrahydroacridin-1-one dihydrochloride (Compound (I) with R¹=R³=H, R²=—NH₂, A=>C=CH(CH₂)ₙ—, Y=>C=O, m=2, and n=2).

¹H-NMR δ ppm (DMSO-d₆) 8.77(b. d, 1H), 8.11(m, 1H), 8.03(m, 1H), 7.69(m, 3H), 7.46(m, 3H), 4.83(b. t, 1H), 4.23(b. s, 2H), 3.6-2.6(m, 10H), 2.4-1.2(m, 7H).

IR ν KBr$_{max}$ cm⁻¹: 1630.

Example 44

9-Amino-2-(3-(1-benzylpiperidin-4-yl)propyl)-1,2,3,4-tetrahydroacridin-1-one dihydrochloride (Compound (I) with R¹=R³=H, R²=—NH₂, A=>CH(CH₂)ₙ—, Y=>C=O, m=2, and n=3).

¹H-NMR δ ppm (DMSO-d₆) 8.78(b. d, 1H), 8 16(m, 1H), 8.02(m, 1H), 7.70(m, 3H), 7.45(m, 3H), 4.20(b. s, 2H), 3.7-2.6(m, 7H), 2.4-1.2(m, 13H).

IR ν KBr$_{max}$ cm⁻¹: 1630.

Example 45

9-Amino-2-(4-(1-benzylpiperidin-4-yl)butylidene)-1,2,3,4-tetrahydroacridin-1-one dihydrochloride (Compound (I) with R¹=R³=H, R²=—NH₂, A=>C=CH(CH₂)ₙ—, Y=>C=O, m=2, and n=3).

¹H-NMR δ ppm (DMSO-d₆) 8.79 (b. d, 1H), 8.14(m, 1H), 8.03(m, 1H), 7.69(m, 3H), 7.45(m, 3H), 4.86(b. t, 1H), 4.21(b. s, 2H), 3.7-2.7(m, 10H), 2.4-1.2(m, 9H).

IR ν KBr$_{max}$ cm⁻¹: 1630.

Example 46

9-Amino-2-(4-(1-benzylpiperidin-4-yl)butyl)-1,2,3,4-tetrahydroacridin-1-one dihydrochloride (Compound (I) with R¹=R³=H, R²=—NH₂, A=>CH(CH₂)ₙ—, Y=>C=O, m=2, and n=4).

¹H-NMR δ ppm (DMSO-d₆) 8.76(b. d, 1H), 8.13(m, 1H), 8.02(m, 1H), 7.68(m, 3H), 7.45(m, 3H), 4.21(b. s, 2H), 3.7-2.6(m, 7H), 2.4-1.2(m, 15H).

IR ν KBr$_{max}$ cm⁻¹: 1635.

Example 47

9-Amino-2-(1-benzylpiperidin-4-ylidene)-1,2,3,4-tetrahydroacridin-1-one dihydrochloride (Compound (I) with R¹=R³=H, R²=—NH₂, A=>C=, Y=>C=O, and m=2).

¹H-NMR δ ppm (DMSO-d₆) 8.76(b. d, 1H), 8.10(m, 1H), 8.03(m, 1H), 7.70(m, 3H), 7.47(m, 3H), 4.30(b. s, 2H), 3.6-2.6(m, 12H).

IR ν KBr$_{max}$ cm⁻¹: 1630.

Example 48

9-Amino-2-(6-(1-benzylpiperidin-4-yl)hexylidene)-1,2,3,4-tetrahydroacridin-1-one dihydrochloride (Compound (I) with R¹=R³=H, R²=—NH₂, A=>C=CH(CH₂)ₙ—, Y=>C=O, m=2, and n=5).

¹H-NMR δ ppm (DMSO-d₆) 8.77(b. d, 1H), 8.10(m, 1H), 8.03(m, 1H), 7.68(m, 3H), 7.45(m, 3H), 4.86(b. t, 1H), 4.22(b. s, 1H), 3.5-2.6(m, 10H), 2.4-1.1(m, 13H).

IR ν KBr$_{max}$ cm⁻¹: 1630.

Example 49

9-Amino-2-(6-(1-benzylpiperidin-4-yl)hexyl)-1,2,3,4-tetrahydroacridin-1-one dihydrochloride (Compound (I) with R¹=R³=H, R²=—NH₂, A=>CH(CH₂)ₙ—, Y=>C=O, m=2, and n=6).

¹H-NMR δ ppm (DMSO-d₆): 8.78(b. d, 1H), 8.15(m, 1H), 8.00(m, 1H), 7.68(m, 3H), 7.44(m, 3H), 4.19(b. s, 2H), 3.6-2.6(m, 7H), 2.4-1.0(m, 19H).

IR ν KBr$_{max}$ cm⁻¹: 1630.

Example 50

9-Amino-2-(2-(1-benzylpiperidin-4-yl)ethylidene)-8-fluoro-1,2,3,4-tetrahydroacridin-1-one dihydrochloride (Compound (I) with R¹=8—F, R²=—NH₂, R³=H, A=>C=CH(CH₂)ₙ—, Y=>C=O, m=2, and n=1).

¹H-NMR δ ppm (DMSO-d₆): 8.03(m, 2H), 7.66(m, 3H), 7.45(m, 3H), 4.92(m, 1H), 4.22(b. s, 2H), 3.7-2.6(m, 10H), 2.4-1.6(m, 5H).

IR ν KBr$_{max}$ cm⁻¹: 1640.

Example 51

9-Amino-2-(2-(1-benzylpiperidin-4-yl)ethyl)-8-fluoro-1,2,3,4-tetrahydroacridin-1-one dihydrochloride (Compound (I) with R¹=8—F, R²=—NH₂, R³=H, A=>CH(CH₂)ₙ—, Y=>C=O, m=2, and n=2).

¹H-NMR δ ppm (DMSO-d₆): 8.01(m, 2H), 7.65(m, 3H), 7.45(m, 3H), 4.21(b. s, 2H), 3.5-2.6(m, 7H), 2.4-1.2(m, 11H).

IR ν KBr$_{max}$ cm⁻¹: 1630.

Example 52

9-Amino-2-(4-(1-benzylpiperidin-4-yl)butylidene)-8-fluoro-1,2,3,4-tetrahydroacridin-1-one dihydrochloride (Compound (I) with R¹=8—F, R²=—NH₂, R³=H, A=>C=CH(CH₂)ₙ—, Y=>C=O, m=2, and n=3).

¹H-NMR δ ppm (DMSO-d₆): 8.02(m, 2H), 7.64(m, 3H), 7.45(m, 3H), 4.86(m, 1H), 4.22(b. s, 1H), 3.7-2.6(m, 10H), 2.4-1.2(m, 9H).

IR ν KBr$_{max}$ cm⁻¹: 1635.

Example 53

11-Amino-2-(2-(1-benzylpiperidin-4-yl)ethylidene)-2,3,4,5-tetrahydrocyclohepta[b]quinolin-1-one dihydrochloride (Compound (I) with R¹=R³=H, R²=—NH₂, A=>C=CH(CH₂)ₙ—, Y=>C=O, m=3, and n=1).

¹H-NMR δ ppm (DMSO-d₆): 8.76(b. d, 1H), 8.22(m, 1H), 8.02(m, 1H, 7.69(m, 3H), 7.46(m, 3H), 6.80(t, 1H), 4.24(m, 2H), 3.5-2.7(m, 10H), 2.4-1.4(m, 7H).

IR ν KBr$_{max}$ cm⁻¹: 1630.

Example 54

0.41 gm of 9-amino-2-(2-(1-benzylpiperidin-4-yl)ethyl)-1,2,3,4-tetrahydroacridin-1-one was dissolved into 10 ml of methanol. To the solution was added 0.15 gm of sodium borohydride, and the mixture was stirred for 2 hours at room temperature. After the addition of 30 ml of water, the reaction mixture was extracted with chloroform. The extract was washed with saturated brine, dried, and evaporated under reduced pressure. 0.28 gm of 9-amino-2-(2-(1-benzylpiperidin-4-yl)ethyl]-1,2,3,4-tetrahydroacridin-1-ol (Compound (I) with R¹=R³=H, R²=—NH₂, A=>CH(CH₂)ₙ—, Y=>CHOH, m=2, and n=2) was obtained by recrystallizing the residue from ethyl acetate.

mp: 184°-186° C.

¹H-NMR δ ppm (CDCl₃) 7.83(m, 1H), 7.69(m, 1H), 7.46(m, 1H), 7.30(s, 5H), 7.3(m, 1H), 5.5(m, 1H), 4.7(m, 1H), 3.48(s, 2H), 2.9(m, 4H), 2.1–1.1(m, 14H).

Example 55

To 1.74 gm of 9-aminofuro[3,4-b]quinolin-1(3H)-one was added 3.20 gm of 4-aminobutyl-1-benzylpiperidine, and the mixture was heated in a sealed tube for 6 hours at 200° C. while stirring. After cooling, the reaction mixture was recrystallized from ethyl acetate to obtain 3.00 gm of 9-amino-2-(4-(1-benzylpiperidyl)butyl)-2,3-dihydropyrrolo-[3,4-b]quinolin-1-one (Compound (I) with $R^1=R^3=H$, $R^2=NH_2$, $A=>N-(CH_2)_n-$, $Y=>C=O$, $m=1$, and $n=4$).

mp: 140°–142° C.

¹H-NMR δ ppm (CDCl₃) 7.95(m, 2H), 7.75(m, 1H), 7.48(m, 1H), 7.33(s, 5H), 6.52(br, 2H), 4.39(s, 2H), 3.59(t, 2H), 3.53(s, 2H), 2.89(b. d, 2H), 2.1–1.1(m, 13H).

IR ν KBr$_{max}$ cm⁻¹: 1675, 1640.

The compounds of Examples 56–60 were prepared in the same manner as in Example 55.

Example 56

9-Amino-8-fluoro-2-(4-(1-benzylpiperidyl)ethyl)-2,3-dihydropyrrolo[3,4-b]quinolin-1-one (Compound (I) with $R^1=8-F$, $R^2=NH_2$, $R^3=H$, $A=>N-(CH_2)_n-$, $Y=>C=O$, $m=1$, and $n=2$).

mp: 134°–136° C.

¹H-NMR δ ppm (CDCl₃) 7.70(m, 2H), 7.31(s, 5H), 7.06(m, 1H), 6.45(br, 2H), 4.33(s, 2H), 3.61(t, 2H), 3.50(s, 2H), 2.89(b. d, 2H), 2.1–1.2(m, 9H).

IR ν KBr$_{max}$ cm⁻¹: 1655, 1620.

Example 57

9-Amino-8-methylthio-2-(4-(1-benzylpiperidyl)ethyl)-2,3-dihydropyrrolo[3,4-b]quinolin-1-one (Compound (I) with $R^1=8-SCH_3$, $R^2=NH_2$, $R^3=H$, $A=>N-(CH_2)_n-$, $Y=>C=O$, $m=1$, and $n=2$).

¹H-NMR δ ppm (CDCl₃) 8.45(br, 2H), 7.89(m, 1H), 7.58(m, 2H), 7.33(s, 5H), 4.31(s, 2H), 3.62(t, 2H), 3.52(s, 2H), 2.91(b. d, 2H), 3.52(s, 3H), 2.1–1.2(m, 9H).

IR ν KBr$_{max}$ cm⁻¹: 1670, 1620.

Example 58

2-(4-(1-benzylpiperidyl)ethyl)-2,3-dihydropyrrolo[3,4-b]quinolin-1-one (Compound (I) with $R^1=R^2=R^3=H$, $A=>N-(CH_2)_n-$, $Y=>C=O$, $m=1$, and $n=2$).

mp: 163°–164° C.

¹H-NMR δ ppm (CDCl₃) 8.65(s, 1H), 8.25–7.55(m, 4H), 7.35 (s, 5H), 4.55(s, 2H), 3.75(t, 2H), 3.59(s, 2H), 2.98(b. d, 2H), 2.2–1.2(m, 9H).

IR ν KBr$_{max}$ cm⁻¹: 1680.

Example 59

9-Methyl-2-(4-(1-benzylpiperidyl)ethyl)-2,3-dihydropyrrolo-3,4-b]quinolin-1-one (Compound (I) with $R^1=R^3=H$, $R^2=CH_3$, $A=>N-(CH_2)_n-$, $Y=>C=O$, $m=1$, and $n=2$).

mp: 113°–114° C.

¹H-NMR δ ppm (CDCl₃): 8.18(m, 2H), 7.84(m, 1H), 7.64(m, 1H), 7.32(s, 5H), 4.46(s, 2H), 3.71(t, 2H), 3.50(s, 2H), 3.14(s, H), 2.89(b. d, 2H), 2.2–1.2(m, 9H).

IR ν KBr$_{max}$ cm⁻¹: 1675.

Example 60

9-Phenyl-2-(4-(1-benzylpiperidyl)ethyl)-2,3-dihydropyrrolo-3,4-b]quinolin-1-one (Compound (I) with $R^1=R^3=H$, $R^2=Ph$, $A=>N-(CH_2)_n-$, $Y=>C=O$, $m=1$, and $n=2$).

mp: 158°–159° C.

¹H-NMR δ ppm (CDCl₃) 8.21(b. d, 1H), 7.84(m, 2H), 7.54(m, 6H), 7.32(s, 5H), 4.55(s, 2H), 3.64(t, 2H), 3.51(s, 2H), 2.82(b. d, 2H), 2.1–1.2(m, 9H).

IR ν KBr$_{max}$ cm⁻¹: 1690.

Example 61

10.1 gm of 9-hydroxyfuro[3,4-b]quinolin-1(3H)-one was suspended into 50 ml of N-methyl-2-pyrrolidone, and to the suspension was added 12.0 gm of 4-aminoethyl-1-benzylpiperidine. The mixture, placed in a reaction vessel equipped with a Dean-Stark water separator, was refluxed on an oil bath at 200°–210° C. for 6 hours while stirring. After cooling, 200 ml of acetone was added to the concentrated reaction mixture. Deposited crystals were collected by filtration recrystallized in a methanol-water mixture to obtain 12.5 gm of 9-hydroxy-2-(4-(1-benzylpiperidyl)ethyl)-2,3-dihydropyrrolo[3,4-b]quinolin-1-one (Compound (I) with $R^1=R^3=H$, $R^2=OH$, $A=>N-(CH_2)_n-$, $Y=>C=O$, $m=1$, and $n=2$).

mp: 259°–261° C (decomposed).

¹H-NMR δ ppm (DMSO-d₆): 12.30(br, 1H), 8.22(b. d, 1H), 7.62(m, 2H), 7.37(m, 1H), 7.29(s, 5H), 4.39(s, 2H), 3.47(s, 2H), 3.42(t, 2H), 2.80(b. d, 2H), 2.1–1.2(m, 9H).

IR ν KBr$_{max}$ cm⁻¹: 1675.

The compounds of Examples 62–66 were prepared in the same manner as in Example 61.

Example 62

6-Chloro-9-hydroxy-2-(4-(1-benzylpiperidyl)ethyl)-2,3-dihydropyrrolo[3,4-b]quinolin-1-one (Compound (I) with $R^1=6-Cl$, $R^2=OH$, $R^3=H$, $A=>N-(CH_2)_n-$, $Y=>C=O$, $m=1$, and $n=2$).

mp: 250° C. (Decomposed).

¹H-NMR δ ppm (DMSO-d₆): 8.20(d, 1H), 7.61(d, 1H), 7.38(d. d, 1H), 7.30(s, 2H), 4.39(s, 2H), 3.47(s, 2H), 3.41(t, 2H), 2.79(b. d, 2H), 2.2–1.2(m, 9H).

IR ν KBr$_{max}$ cm⁻¹: 1690.

Example 63

7-Chloro-9-hydroxy-2-(4-(1-benzylpiperidyl)ethyl)-2,3-dihydropyrrolo[3,4-b]quinolin-1-one (Compound (I) with $R^1=7-Cl$, $R^2=OH$, $R^3=H$, $A=>N-(CH_2)_n-$, $Y=>C=O$, $m=1$, and $n=2$).

mp: 245° C. (Decomposed),

¹H-NMR δ ppm (DMSO-d₆): 8.13(d, 1H), 7.65(m, 2H), 7.29(s, 5H), 4.38(s, 2H), 3.46(s, 2H), 3.42(t, 2H), 2.80(b. d, 2H), 2.1–1.2(m, 9H).

IR ν KBr$_{max}$ cm⁻¹: 1690.

Example 64

9-Hydroxy-8-methylthio-2-(4-(1-benzylpiperidyl)ethyl)-2,3-dihydropyrrolo[3,4-b]quinolin-1-one (Compound (I) with $R^1=8-SCH_3$, $R^2=OH$, $R^3=H$, $A=>N-(CH_2)_n-$, $Y=>C=O$, $m=1$, and $n=2$).

mp: 215° C. (Decomposed).

¹H-NMR δ ppm (DMSO-d₆): 7.53(m, 1H), 7.27(s, 5H), 7.1(m, 2H), 4.31(s, 2H), 3.44(s, 2H), 3.39(t, 2H), 2.78(b. d, 2H), 2.31(s, 3H), 2.1–1.1(m, 9H).

IR ν KBr$_{max}$ cm⁻¹: 1660.

Example 65

9-Hydroxy-2-(4-(1-benzylpiperidyl)methyl)-2,3-dihydropyrrolo[3,4-b]quinolin-1-one (Compound (I) with $R^1=R^3=H$, $R^2=OH$, $A=>N-(CH_2)_n-$, $Y=>C=O$, m=1, and n=1).

$^1$H-NMR δ ppm (DMSO-d$_6$): 8.22(b. d, 1H), 7.63(m, 2H), 7.39(m, 1H), 7.31(s, 5H), 4.42(s, 2H), 3.49(s, 2H), 3.28(d, 2H), 2.81(b d, 2H), 2.1-1.1(m, 7H).

IR ν KBr$_{max}$ cm$^{-1}$: 1680.

Example 66

9-Hydroxy-2-(4-(1-benzylpiperidyl)propyl)-2,3-dihydropyrrolo[3,4-b]quinolin-1-one (Compound (I) with $R^1=R^3=H$, $R^2=OH$, $A=>N-(CH_2)_n-$, $Y=>C=O$, m=1, and n=3).

$^1$H-NMR δ ppm (DMSO-d$_6$): 8.24(b. d, 1H), 7.63(m, 2H), 7.40(m, 1H), 7.28(s, 5H), 4.36(s, 2H), 3.47(s, 2H), 3.36(t, 2H), 2.82(b. d, 2H), 2.2-1.1(m, 11H).

IR ν KBr$_{max}$ cm$^{-1}$: 1675.

Example 67

6.80 gm of 9-hydroxy-2-(4-(1-benzylpiperidyl)ethyl)-2,3-dihydropyrrolo[3,4-b]quinolin-1-one was suspended into 300 ml of methanol. To the suspension was added dropwise a solution of diazomethane in ether at room temperature while stirring until generation of nitrogen gas terminated. The reaction mixture was dried under reduced pressure and the residue was recrystallized in acetonitrile to obtain 5.30 gm of 9-methoxy-2-(4-(1-benzylpiperidyl)ethyl)-2,3-dihydropyrrolo[3,4-b]quinolin-1-one (Compound (I) with $R=R^3=H$, $R^2=OCH_3$, $A=>N-(CH_2)_n-$, $Y=>C=O$, m=1, and n=2).

mp: 98°-99° C.

$^1$H-NMR δ ppm (CDCl$_3$) 8.42(b. d, 1H), 8.04(b. d, 1H), 7.82(m, 1H), 7.56(m, 1H), 7.32(s, 5H), 4.66(s, 3H), 4.47(s, 2H), 3.68(t, 2H), 3.52(s, 2H), 2.92(b. d, 2H), 2.1-1.2(m, 9H).

IR ν KBr$_{max}$ cm$^{-1}$: 1680.

The compounds of Examples 68-72 were prepared in the same manner as in Example 67.

Example 68

6-Chloro-9-methoxy-2-(4-(1-benzylpiperidyl)ethyl)-2,3-dihydropyrrolo[3,4-b]quinolin-1-one (Compound (I) with R=6—Cl, $R^2=OCH_3$, $R^3=H$, $A=>N-(CH_2)_n-$, $Y=>C=O$, m=1, and n=2).

mp: 95°-96° C.

$^1$H-NMR δ ppm (CDCl$_3$) 8.31(d, 1H), 7.98(d, 1H), 7.48(d. d, 1H), 7.32(s, 5H), 4.65(s, 3H), 4.45(s, 2H), 3.65(t, 2H), 3.51(s, 2H), 2.90(b. d, 2H), 2.1-1.2(m, 9H).

IR ν KBr$_{max}$ cm$^{-1}$: 1680.

Example 69

7-Chloro-9-methoxy-2-(4-(1-benzylpiperidyl)ethyl)-2,3-dihydropyrrolo[3,4-b]quinolin-1-one (Compound (I) with $R^1=7$—Cl, $R^2=OCH_3$, $R^3=H$, $A=>N-(CH_2)_n-$, $Y=>C=O$, m=1, and n=2).

mp: 127°-129° C.

$^1$H-NMR δ ppm (CDCl$_3$) 8.38(d, 1H), 7.97(d, 1H), 7.71(d. d, 1H), 7.32(s, 5H), 4.66(s, 3H), 4.46(s, 2H), 3.67(t, 2H), 3.50(s, 2H), 2.89(b. d, 2H), 2.1-1.2(m, 9H).

IR ν KBr$_{max}$ cm$^{-1}$: 1675.

Example 70

9-Methoxy-8-methylthio-2-(4-(1-benzylpiperidyl)ethyl)-2,3-dihydropyrrolo[3,4-b]quinolin-1-one (Compound (I) with $R^1=8$—SCH$_3$, $R^2=OCH_3$, $R^3=H$, $A=>N-(CH_2)_n-$, $Y=>C=O$, m=1, and n=2).

$^1$H-NMR δ ppm (CDCl$_3$) 7.70(m, 2H), 7.31(s, 5H), 7.25(m, 1H), 4.51(s, 3H), 4.44(s, 2H), 3.66(t, 2H), 3.49(s, 2H), 2.87(b. d, 2H), 2.49(s, 3H), 2.1-1.2(m, 9H).

IR ν KBr$_{max}$ cm$^{-1}$: 1680.

Example 71

9-Methoxy-2-(4-(1-benzylpiperidyl)methyl)-2,3-dihydropyrrolo[3,4-b]quinolin-1-one (Compound (I) with $R^1=R^3=H$, $R^2=OCH_3$, $A=>N-(CH_2)_n-$, $Y=>C=O$, m=1, and n=1).

mp: 133°-135° C.

$^1$H-NMR δ ppm (CDCl$_3$): 8.41(b. d, 1H), 8.03(b. d, 1H), 7.80(m, 1H), 7.54(m, 1H), 7.31(s, 5H), 4.65(s, 3H), 4.50(s, 2H), 3.52(d, 2H), 3.49(s, 2H), 2.88(b. d, 2H), 2.1-1.2(m, 7H).

IR ν KBr$_{max}$ cm$^{-1}$: 1675.

Example 72

9-Methoxy-2-(4-(1-benzylpiperidyl)propyl)-2,3-dihydropyrrolo[3,4-b]quinolin-1-one (Compound (I) with $R^1=R^3=H$, $R^2=OCH_3$, $A=>N-(CH_22)_n-$, $Y=>C=O$, m=1, and n=3).

$^1$H-NMR δ ppm (CDCl$_3$) 8.42(b. d, 1H), 8.03(b. d, 1H), 7.82(m, 1H), 7.55(m, 1H), 7.32(s, 5H), 4.66(s, 3H), 4.48(s, 2H), 3.61(t, 2H), 3.49(s, 2H), 2.87(b. d, 2H), 2.1-1.1(m, 11H).

IR ν KBr$_{max}$ cm$^{-1}$: 1685.

Example 73

To 0.21 gm of 9-methoxy-2-(4-(1-benzylpiperidyl)ethyl)-2,3-dihydropyrrolo[3,4-b]quinolin-1-one was added 10 ml of butylamine, and the mixture was refluxed for 3 hours while stirring. The reaction mixture was dried under reduced pressure and the residue was recrystallized in acetone to obtain 0.21 gm of 9-n-butylamino-2-(4-(1-benzylpiperidyl)ethyl)-2,3-dihydropyrrolo[3,4-b]quinolin-1-one (Compound (I) with $R^1=R^3=H$, $R^2=NH$—n—butyl, $A=>N-(CH_2)_n-$, $Y=>C=O$, m=1, and n=2).

mp: 145°-146° C.

$^1$H-NMR δ ppm (CDCl$_3$) 8.34(b. d, 1H), 8.07(br, 1H), 7.95(b. d, 1H), 7.70(m, 1H), 7.40(m, 1H), 7.32(s, 5H), 4.33(s, 2H), 3.87(m, 2H), 3.61(t, 2H), 3.50(s, 2H), 2.90(b. d, 2H), 2.2-1.2(m, 13H), 0.99(t, 3H).

IR ν KBr$_{max}$ cm$^{-1}$: 1640.

The compounds of Examples 74-75 were prepared in the same manner as in Example 73.

Example 74

9-Methylamino-2-(4-(1-benzylpiperidyl)ethyl)-2,3-dihydropyrrolo[3,4-b]quinolin-1-one (Compound (I) with $R^1=R^3=H$, $R^2=NHCH_3$, $A=>N-(CH_2)_n-$, $Y=>C=O$, m=1, and n=2).

mp: 141°-142° C.

$^1$H-NMR δ ppm (CDCl$_3$) 8.40(b. d, 1H), 8.14(br, 1H), 7.93(b. d, 1H), 7.67(m, 1H), 7.36(m, 1H), 7.29(s, 5H), 4.28(s, 2H), 3.57(t, 2H), 3.52(s, 2H), 3.47(d, 3H), 2.90(b. d, 2H), 2.1-1.2(m, 9H).

IR ν KBr$_{max}$ cm$^{-1}$: 1650.

Example 75

9-(4-(1-Benzylpiperidyl)ethylamino)-2-(4-(1-benzylpiperidyl)ethyl)-2,3-dihydropyrrolo[3,4-b]quinolin-1-one (Compound (I) with $R^1=R^3=H$,

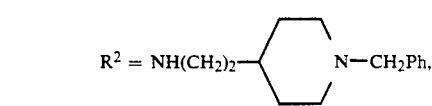

$A=>N-(CH_2)_n-$, $Y=>C=O$, m=1, and n=2).

¹H-NMR δ ppm (CDCl₃): 8.30(b. d, 1H), 8.00(br, 1H), 7.94(b. d, 1H), 7.68(m, 1H), 7.38(m, 1H), 7.30(s, 10H), 4.31(s, 2H), 3.86(m, 2H), 3.59(t, 2H), 3.49(s, 4H), 2.89(b. d, 4H), 2.4–1.2(m, 18H).

Example 76

0.30 gm of 9-amino-2-(4-(1-benzylpiperidyl)ethyl)-2,3-dihydropyrrolo[3,4-b]quinolin-1-one was dissolved into 5 ml of pyridine. To the solution was added 3 ml of acetic anhydride and the mixture was refluxed for 3 hours while stirring. After cooling, the reaction mixture was poured into ice water and extracted with ethyl acetate. After the addition of 30 ml of ammonia water to the organic layer, the mixture was stirred at room temperature for 15 hours. The organic layer was separated, dried, and evaporated under reduced pressure. The residue was subjected to silica gel column chromatography to obtain crystals from a fraction eluted with chloroform-methanol (100:1). The crystals were recrystallized in isopropyl ether to obtain 0.19 gm of N-(2-(4-(1-benzylpiperidyl)-ethyl)-2,3-dihydro-1-oxopyrrolo[3,4-b]quinolin-9-yl) acetamide. (Compound (I) with $R^1=R^3=H$, $R^2=NHCOCH_3$, $A=>N-(CH_2)_n-$, $Y=>C=O$, m=1, and n=2).

mp: 109°–111° C.

¹H-NMR δ ppm (CDCl₃): 9.70(b. s, 1H), 8.09(m, 2H), 7.84(m, 1H), 7.58(m, 1H), 7.37(s, 5H), 4.49(s, 2H), 3.70(t, 2H), 3 67(s, 2H), 3.05(b. d, 2H),2.39(s, 3H), 2.3–1.2(m, 9H).

IR ν KBr$_{max}$ cm⁻¹: 1690, 1630.

Example 77

0.80 gm of 9-hydroxy-2-(4-(1-benzylpiperidyl)ethyl)-2,3-dihydropyrrolo[3,4-b]quinolin-1-one was suspended into 40 ml of dichloromethane. To the suspension were added 0.30 gm of N,N-diethylaniline 10 ml of phosphorus oxychloride, and the mixture was stirred for 15 hours at room temperature. The reaction mixture was dried under reduced pressure. The residue was partitioned with chloroform and water. The chloroform layer was dried and evaporated under reduced pressure. The residue was subjected to silica gel column chromatography to obtain crystals from a fraction eluted with chloroform-methanol (30:1). The crystals were recrystallized in an isopropyl ether-acetone mixture to obtain 0.70 gm of 9-chloro-2-(4-(1-benzylpiperidyl)ethyl)-2,3-dihydropyrrolo[3,4-b]quinolin-1-one. (Compound (I) with $R^1=R^3=H$, $R^2=Cl$, $A=>N-(CH_2)_n-$, $Y=>C=O$, m=1, and n=2).

mp: 63°–65° C.

¹H-NMR δ ppm (CDCl₃): 8.50(b. d, 1H), 8.17(b. d, 1H), 7.91(m, 1H), 7.73(m, 1H), 7.32(s, 5H), 4.50(s, 2H), 3.74(t, 2H), 3.50(s, 2H), 2.90(b. d, 2H), 2.2–1.2(m, 9H).

IR ν KBr$_{max}$ cm⁻¹: 1690.

Example 78

0.50 gm of 9-chloro-2-(4-(1-benzylpiperidyl)ethyl)-2,3-dihydropyrrolo[3,4-b]quinolin-1-one was dissolved into 5 ml of ethanol. To the solution was added 5 ml of 1M sodium ethylate solution in ethanol, and the mixture was stirred for 1 hour at room temperature. The reaction mixture was poured into 40 ml of ice water and extracted with chloroform. The chloroform layer was washed with saturated brine, dried, and evaporated under reduced pressure. The residue was subjected to silica gel column chromatography to obtain crystals from a fraction eluted with chloroform-methanol (30:1). The crystals were recrystallized isopropyl ether to obtain 0.33 gm of 9-ethoxy-2-(4-(1-benzylpiperidyl)ethyl)-2,3-dihydropyrrolo[3,4-b]quinolin-1-one. (Compound (I) with $R^1=R^3=H$, $R^2=OCH_2CH_3$, $A=>N-(CH_2)_n-$, $Y=>C=O$, m=1, and n=2).

mp: 117°–119° C.

¹H-NMR δ ppm (CDCl₃): 8.44(b. d, 1H), 8.03(b. d, 1H), 7.81(m, 1H), 7.55(m, 1H), 7.32(s, 5H), 5.07(q, 2H), 4.47(s, 2H), 3.67(t, 2H), 3.48(s, 2H), 2.88(b. d, 2H), 2.2–1.2(m, 9H).

IR ν KBr$_{max}$ cm⁻¹: 1680.

Obviously, numerous modifications and variations of the present invention are possible in light of the above teachings. It is therefore to be understood that within the scope of the appended claims, the invention may be practiced otherwise than as specifically described herein.

What is claimed is:

1. A quinoline compound represented by the following formula (I):

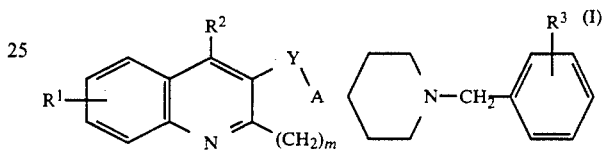

wherein $>A-$ represents a group $>C=$, $>C=CH(CH_2)_n-$, or $>CH(CH_2)_n-$, wherein n is an integer of 0-7; Y represents a group $>C=O$ or $>CHOH$, $R^1$ is a hydrogen atom, a halogen atom, an alkyl group, an alkoxy group, or an alkylthio group, $R^2$ is a hydrogen atom, a halogen atom, an alkyl group, a hydroxy group, an alkoxy group, a phenyl group which may have a substituent, a phenoxy group, an alkanoyloxy group, or an amino group which may have a substituent, $R^3$ is a hydrogen atom, a halogen atom, an alkyl group, or an alkoxy group, and m is an integer of 1-3; or a salt thereof; or wherein $>A-$ represents a group $>N-(CH_2)_n-$, when m=3, and $R^1$, $R^2$, n, Y and $R^3$ are as described above.

2. The quinoline compound of claim 1, wherein $>A-$ represents a group $>C=$, $>C=CH(CH_2)_n-$, or $>CH(CH_2)_n-$, wherein n is an integer of 0-7; Y represents a group $>C=O$ or $>CHOH$, $R^1$ is a hydrogen atom, a halogen atom, an alkyl group, an alkoxy group, or an alkylthio group, $R^2$ is a hydrogen atom, a halogen atom, an alkyl group, a hydroxy group, an alkoxy group, a phenyl group which may have a substituent, a phenoxy group, an alkanoyloxy group, or an amino group which may have a substituent, $R^3$ is a hydrogen atom, a halogen atom, an alkyl group, or an alkoxy group, and m is an integer of 1-3; or a salt thereof.

3. A composition for inhibiting acetylcholinesterase comprising the quinoline compound or its salt as defined in claim 1 and a pharmaceutically acceptable carrier.

4. A method for treating dementia comprising administering an effective dose of the quinoline compound or its salt as defined in claim 1 to a person suffering from or under the risks of suffering from demenita.

* * * * *

UNITED STATES PATENT AND TRADEMARK OFFICE
CERTIFICATE OF CORRECTION

PATENT NO. : 5,240,934
DATED : August 31, 1993
INVENTOR(S) : Hiroshi Hasegawa et al It is certified that error appears in the above-indentified patent and that said Letters Patent is hereby corrected as shown below:

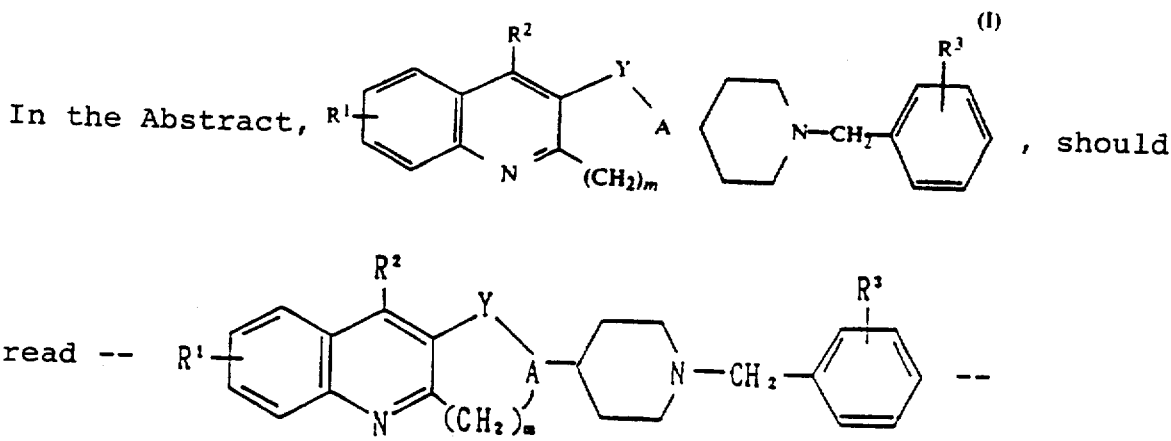

UNITED STATES PATENT AND TRADEMARK OFFICE
CERTIFICATE OF CORRECTION

PATENT NO. : 5,240,934

DATED : August 31, 1993

INVENTOR(S) : Hiroshi Hasewaga et al

It is certified that error appears in the above-indentified patent and that said Letters Patent is hereby corrected as shown below:

Column 2, lines 1-9, " 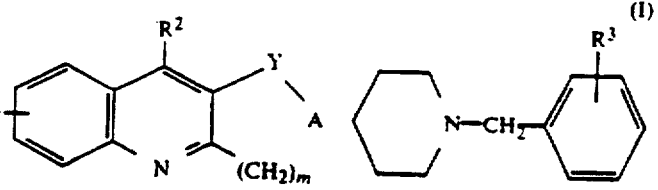 "

should read -- 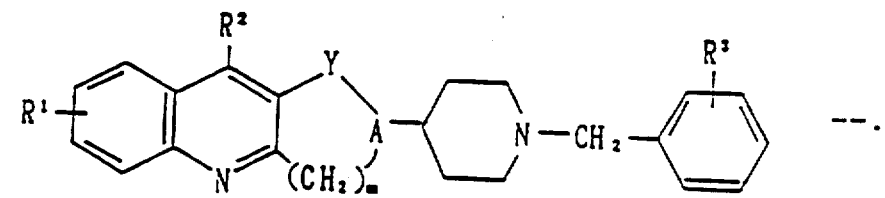 --.

UNITED STATES PATENT AND TRADEMARK OFFICE
CERTIFICATE OF CORRECTION

PATENT NO. : 5,240,934

DATED : August 31, 1993

INVENTOR(S) : Hiroshi Hasegawa et al

It is certified that error appears in the above-indentified patent and that said Letters Patent is hereby corrected as shown below:

Column 36, lines 22-30, " 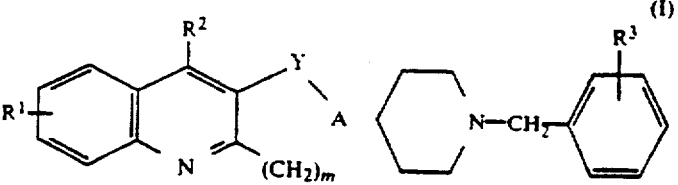 "

should read -- 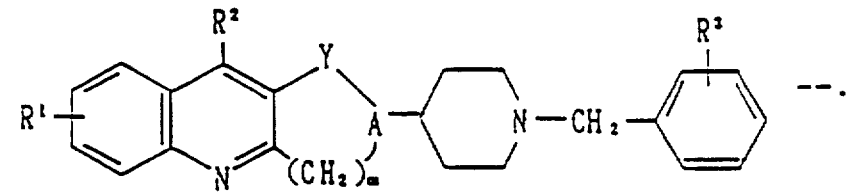 --.

Signed and Sealed this

Twenty-fifth Day of April, 1995

Attest:

BRUCE LEHMAN

Attesting Officer

Commissioner of Patents and Trademarks